United States Patent
Savage et al.

(10) Patent No.: US 11,117,978 B2
(45) Date of Patent: Sep. 14, 2021

(54) CYCLODEXTRIN

(71) Applicant: Curadev Pharma Pvt Ltd, Noida (IN)

(72) Inventors: Tammy Savage, Chatham Maritime (GB); Stephen Wicks, Chatham Maritime (GB); John Mitchell, Chatham Maritime (GB)

(73) Assignee: Curadev Pharma Pvt Ltd, Noida (IN)

( * ) Notice: Subject to any disclaimer, the term of this patent is extended or adjusted under 35 U.S.C. 154(b) by 107 days.

(21) Appl. No.: 14/333,417

(22) Filed: Jul. 16, 2014

(65) Prior Publication Data

US 2015/0025023 A1    Jan. 22, 2015

Related U.S. Application Data

(60) Provisional application No. 61/847,509, filed on Jul. 17, 2013.

(51) Int. Cl.
| | | |
|---|---|---|
| *A61K 31/506* | (2006.01) | |
| *A61K 45/06* | (2006.01) | |
| *A61K 47/40* | (2006.01) | |
| *C08B 37/16* | (2006.01) | |
| *A61K 9/00* | (2006.01) | |
| *A61K 47/69* | (2017.01) | |

(52) U.S. Cl.
CPC ........ *C08B 37/0012* (2013.01); *A61K 9/0019* (2013.01); *A61K 31/506* (2013.01); *A61K 47/40* (2013.01); *A61K 47/6951* (2017.08)

(58) Field of Classification Search
CPC .... A61K 31/506; A61K 45/06; A61K 9/0019; A61K 47/48969; C08B 37/0012
USPC .......................... 514/21.9, 777, 256; 536/120
See application file for complete search history.

(56) References Cited

U.S. PATENT DOCUMENTS

| | | | | |
|---|---|---|---|---|
| 5,134,127 | A * | 7/1992 | Stella ...................... | B82Y 5/00 514/58 |
| 5,376,645 | A | 12/1994 | Stella et al. | |
| 5,874,418 | A | 2/1999 | Stella et al. | |
| 6,153,746 | A * | 11/2000 | Shah .................... | C08B 37/0012 536/103 |
| 6,337,380 | B1 * | 1/2002 | Sasaki ................... | C08F 212/14 430/522 |
| 6,632,803 | B1 | 10/2003 | Harding | |
| 7,635,773 | B2 | 12/2009 | Antle | |
| 2009/0012042 | A1 | 1/2009 | Ren et al. | |
| 2009/0270348 | A1 | 10/2009 | Antle | |
| 2010/0292268 | A1 * | 11/2010 | Mosher ................ | A61K 9/0019 514/301 |
| 2013/0303465 | A1 | 11/2013 | Lewis et al. | |

FOREIGN PATENT DOCUMENTS

| | | | | |
|---|---|---|---|---|
| EP | 0889056 | A2 * | 1/1999 | ............ C08B 37/16 |
| EP | 1 950 227 | B1 | 10/2014 | |
| WO | WO 2003/092590 | A2 | 11/2003 | |
| WO | WO 2009/134347 | A2 | 11/2009 | |
| WO | WO 2013/123254 | A1 | 8/2013 | |

OTHER PUBLICATIONS

Zia et al, Journal of Pharmaceutical Sciences, 1997, 86(2), 220-224.*
Luna et al, Carbohydrate Research, 1997, 299, 103-110.*
Yang et al, Huaxue Shijie Chemical World, Feb. 2013, 54(2), 110-113.*
Search Report from UK Intellectual Property Office, in GB1312737.8, dated Nov. 28, 2013, 4 pages.
Further Search Report from UK Intellectual Property Office, in GB1312737.8, dated Feb. 26, 2014, 2 pages.
Szemán et al., Characterization of Randomly Substituted Anionic Cyclodextrin Derivatives With Different Analytical Methods (2012) *16th International Cyclodextrin Symposium*, Tianjin, China, 1 page.
Szemán et al., Novel stationary phases for high-performance liquid chromatography analysis of cyclodextrin derivatives (2006) *J Chromatogr A*. 1116:76-82.
Brewster et al., "Cyclodextrins as pharmaceutical solubilizers", *Advanced Drug Delivery Reviews*, 2007, vol. 59, pp. 645-666.
Harata et al., "Crystal Structures of Permethylated β-cyclodextrin Complexes with R-(-)- and S-(+)- Flurbiprofen", *Chemistry Letters; The Chemical Society of Japan*, 1984, pp. 1549-1552.
Liu et al., "Complexation of 6-ACYL-O-β-Cyclodextrin derivatives with steroids-effects of chain length and substitution degree", *Drug Development and Industrial Pharmacy*, 1992, vol. 18, No. 15, pp. 1599-1612.
Loftsson et al.; "Cyclodextrins and their pharmaceutical applications," *International Journal of Pharmaceutics*, 2007, vol. 329, No. 1, pp. 1-11.
McQuade et al. "Applying Flow Chemistry: Methods, Materials, and Multistep Synthesis", *The Journal of Organic Chemistry*, Jun. 13, 2013, vol. 78, pp. 6384-6389.
Ou et al., "Some Pharmaceutical Properties of 2,3,6-partially Methylated-β-cyclodextrin and its Solubilizing and Stabilizing Abilities", *Drug Development and Industrial Pharmacy*, 1994, vol. 20, No. 12, pp. 2005-2016.
Rao et al., "Distribution of substituents in O-(2-hydroxypropyl) derivatives of cyclomalto-oligosaccharides (cyclodextrins): influence of increasing substitution, of the base used in the preparation, and of macrocyclic size", *Carbohydrate Research*, 1992, vol. 223, pp. 99-107.

(Continued)

*Primary Examiner* — Ganapathy Krishnan
(74) *Attorney, Agent, or Firm* — Squire Patton Boggs (US) LLP

(57) ABSTRACT

The invention provides a method for preparing sulphoalkyl ether-β-cyclodextrin. The method comprises first contacting cyclodextrin with a base to form activated cyclodextrin. The method then comprises separately contacting the activated cyclodextrin with an alkyl sultone to form sulphoalkyl ether-β-cyclodextrin. The activation reaction is carried in batch and the sulphoalkylation reaction is carried out under continuous flow conditions.

11 Claims, 16 Drawing Sheets

(56) References Cited

OTHER PUBLICATIONS

Stella et al., "Cyclodextrins", *Toxicologic Pathology*, 2008, vol. 36, No. 1, pp. 30-42.
Tait et al., "Characterization of sulphoalkyl ether derivatives of β-cyclodextrin by capillary electrophoresis with indirect UV detection", *Journal of Pharmaceutical & Biomedical Analysis*, 1992, vol. 10, No. 9, pp. 615-622.
Luna et al., "Evaluation of the utility of capillary electrophoresis for the analysis of sulfobutyl ether β-cyclodextrin mixtures", *Journal of Pharmaceutical and Biomedical Analysis*, 1996, vol. 15, pp. 63-71.
Luna et al., "Isolation and characterization by NMR spectroscopy of three monosubstituted 4-sulfobutyl ether derivatives of cyclomaltoheptaose (β-cyclodextrin)", *Carbohydrate Research*, 1997, vol. 299, pp. 111-118.
Ma et al., "The synthesis and process optimization of sulfobutyl ether B-cyclodextrin derivatives", Tetrahedron, vol. 72, 3105-3112, http://dx.doi.org/10.1016/j.tet.2016.04.039 (2016).
Communication of a Notice of Opposition for European Patent Application No. 14742322.2, communication dated Jan. 1, 2019, 24 pages.
Grard et al. "Analysis of sulfobutyl ether-beta-cyclodextrin mixtures by ion-spray mass spectrometry and liquid chromatography-ion-spray mass spectrometry", Journal of Chromatography A. Aug. 3, 2001; 925(1-2):79-87.
Hartman et al., "Deciding whether to go with the flow: evaluating the merits of flow reactors for synthesis" Angew Chem Int Ed Engl. Aug. 8, 2011;50(33):7502-19. doi: 10.1002/anie.201004637. Epub Jun. 27, 2011.
Zannou et al. "Osmotic properties of sulfobutylether and hydroxypropyl cyclodextrins", Pharm Res. Aug. 2001;18(8):1226-31.
Zia et al., "Thermodynamics of binding of neutral molecules to sulfobutyl ether beta-cyclodextrins (SBE-beta-CDs): the effect of total degree of substitution", Pharm Res. Aug. 2000;17(8):936-41.
1,4-butane sultone, CAS No. 1633-83-6; pp. 1-3.
Henson et al., "Adaptive Nonlinear Control of a pH Neutralization Process", IEEE Transations on Control Systems Technology, vol. 2, No. 3, Aug. 1994.
Rajewski, "Development and evaluation of the usefulness and parental safety of modified cyclodextrins", University of Kansas, 1990.
Response submitted by applicant to the European Patent Office dated May 24, 2017, 13 pages.
Response submitted by applicant to the European Patent Office dated Jun. 28, 2016, 17 pages.
Standard Guide for Application of Continuous Processing in the Pharmaceutical Industry, Designation: E2968-14, 15 pages.
Thermo Scientific pH Measurement Handbook, 17 pages.
The Ionic Product for Water, Kw; downloaded from https://www.chemguide.co.uk/physical/acidbaseeqia/kw.html; May 16, 2019, 5 pages.
Brief Communication by Opponent to European Patent Application No. 14742322.2, dated Feb. 21, 2020, 72 pages.
Curriculum Vitae for Stephen Richard Wicks, 6 pages, dated Feb. 2020.
Declaration by Dr. Vincent Antle, 7 pages, dated Feb. 14, 2020.
Declaration of Jeff Duke M.Sc., C. Chem., C.Sci., FRSC, 7 pages, dated May 17, 2019.
Curriculum Vitae for Jeff Duke (Exhibit 1) dated May 17, 2019, 3 pages.
Penry et al., "Chemical Reactor Analysis and Optimal Digestion", BioScience, vol. 36, No. 5, pp. 310-315, May 1986, DOI: 10.2307/1310235.
Guy Furness, Partnering with Big-Pharma: Pfizer & CyDex's Positive Experience: A Case Study: Drug Delivery Technology, vol. 6, No. 1, pp. 54-56, Jan. 2006.
Yang et al., Huaxue Shijie Chemical World, 54(2) (2013) 110-113, "Study on the Synthesis Technology of Sulfobutyl Ether-β-Cyclodextrins with Different Substitution Degree", with English Translation, 12 pages.
First Examination Report for India Patent Application No. 201617003648, 5 pages with translation, dated Aug. 28, 2020.
"Reliable Measurements in a Continuous Flow Baffled Reactor", Source: Mettler-Toledo AG, Process Analytics, Inc., Aug. 27, 2009, Article 1 page.

\* cited by examiner

Figure: 1
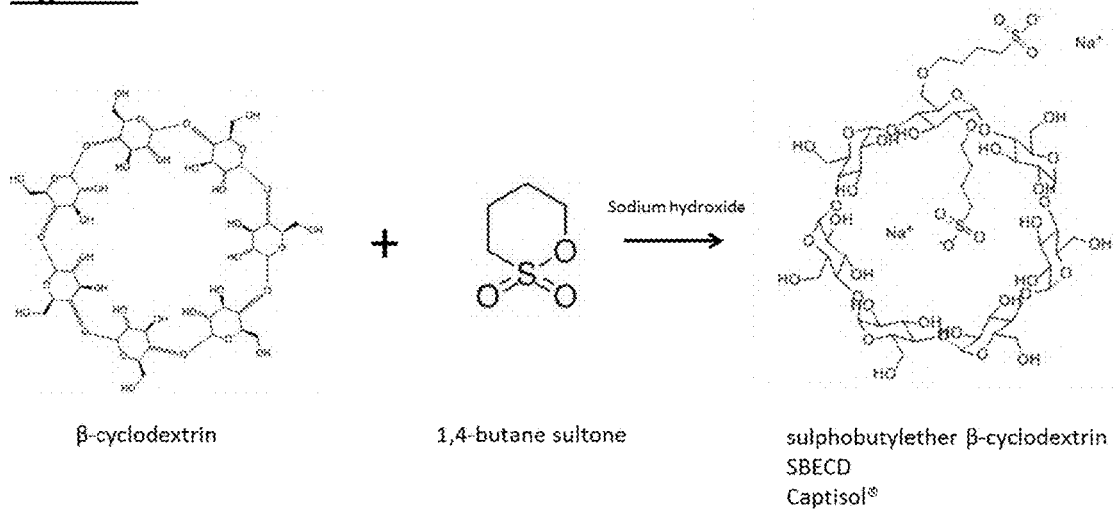
Figure: 2
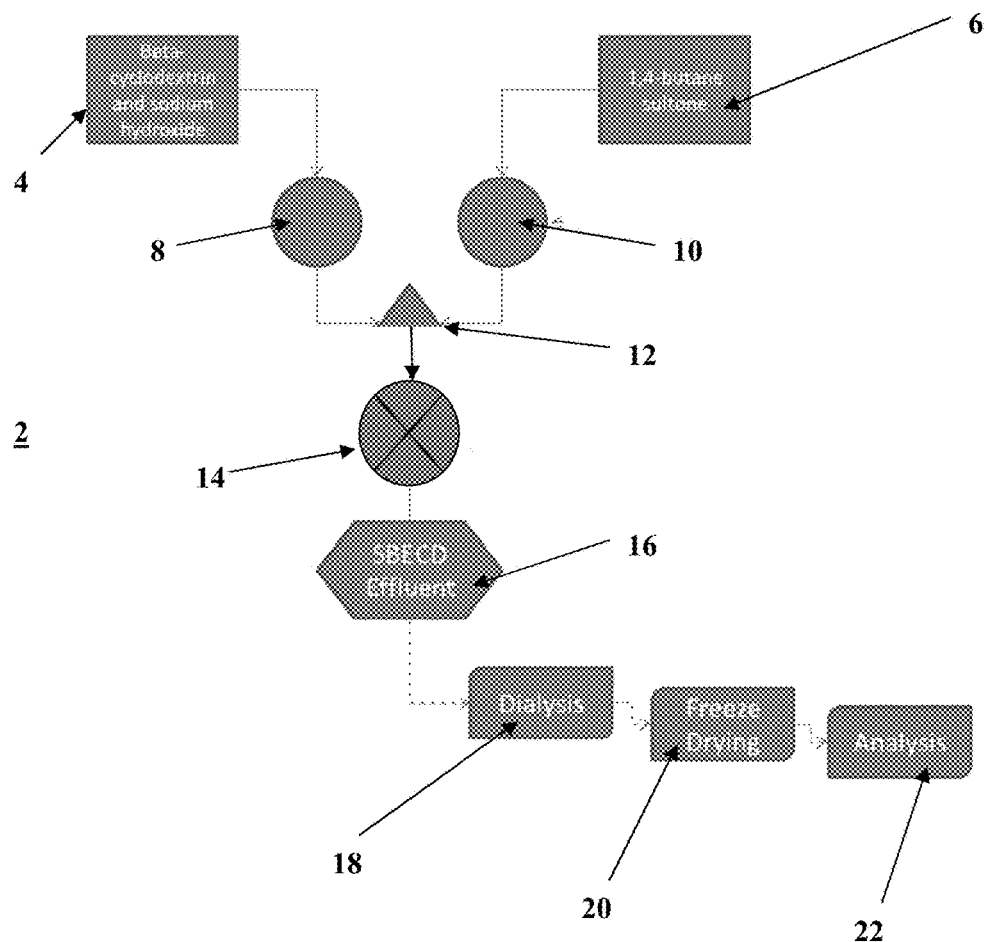

Figure: 5
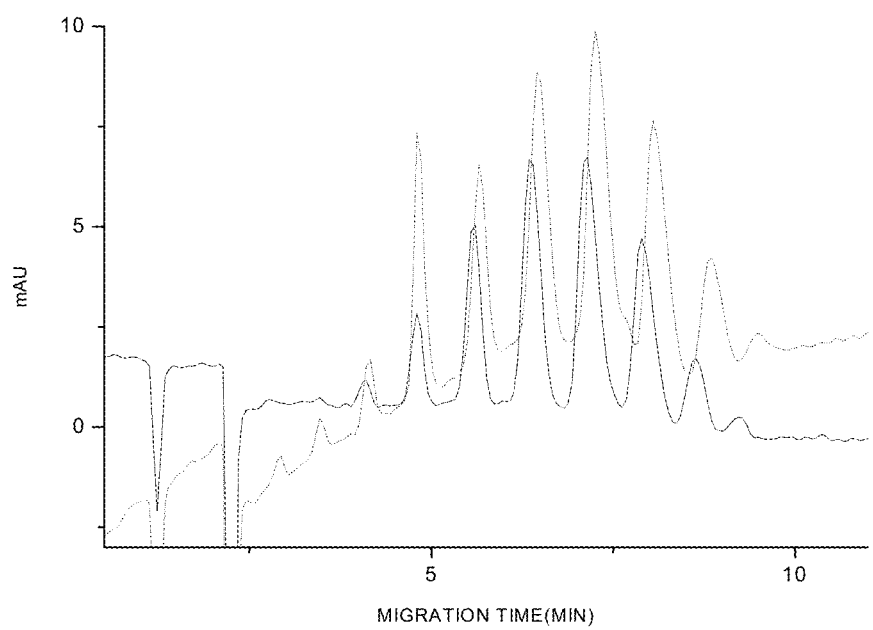
Figure: 6
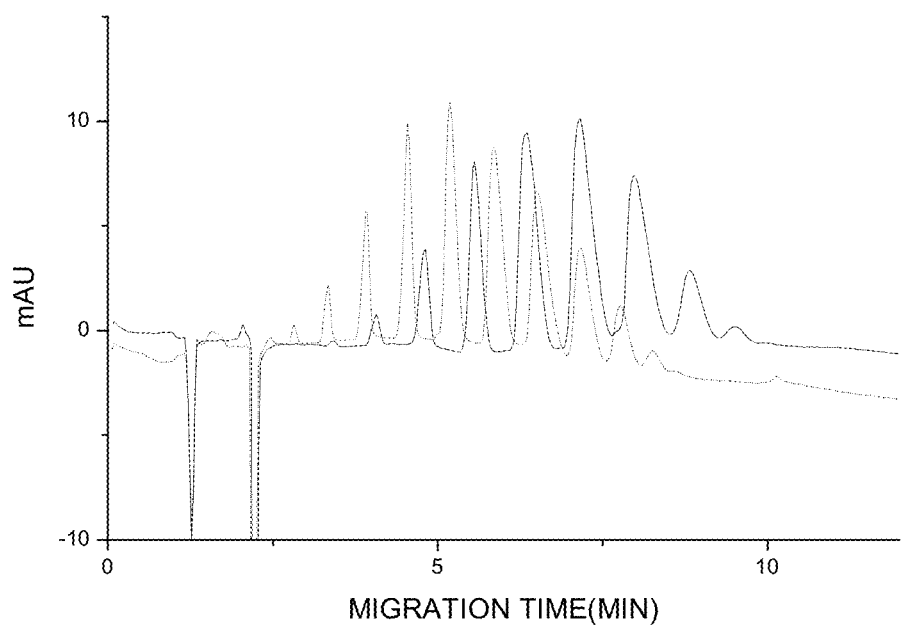

Figure: 7
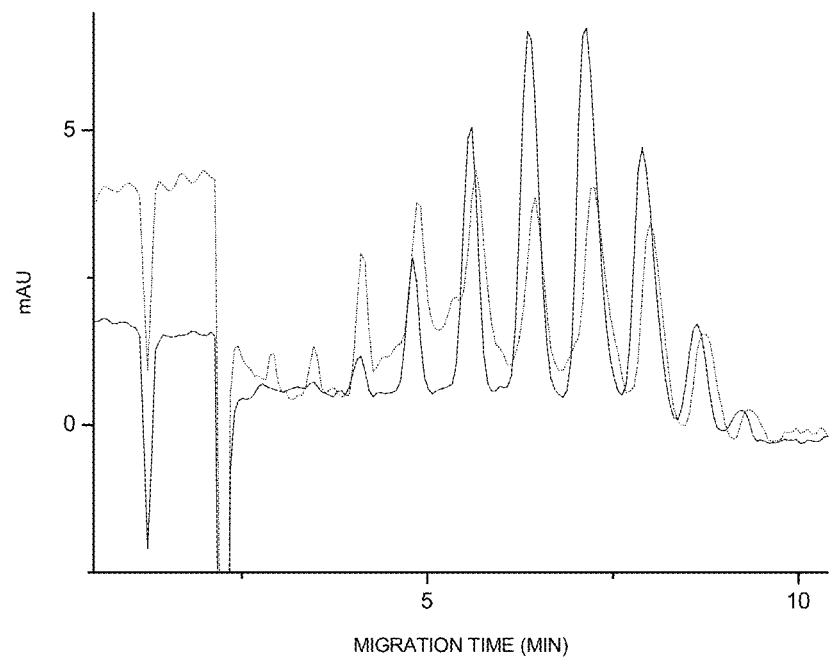
Figure: 8
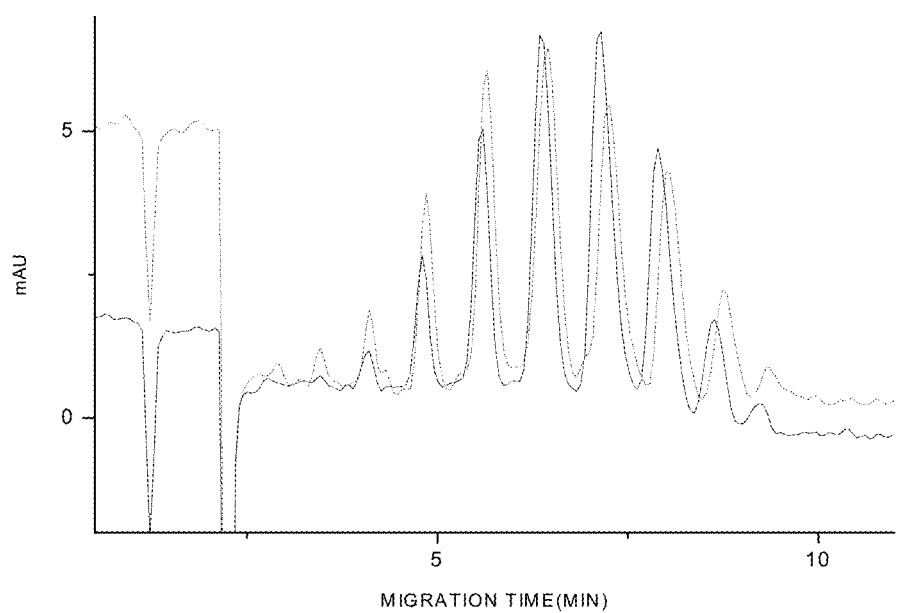

Figure: 9
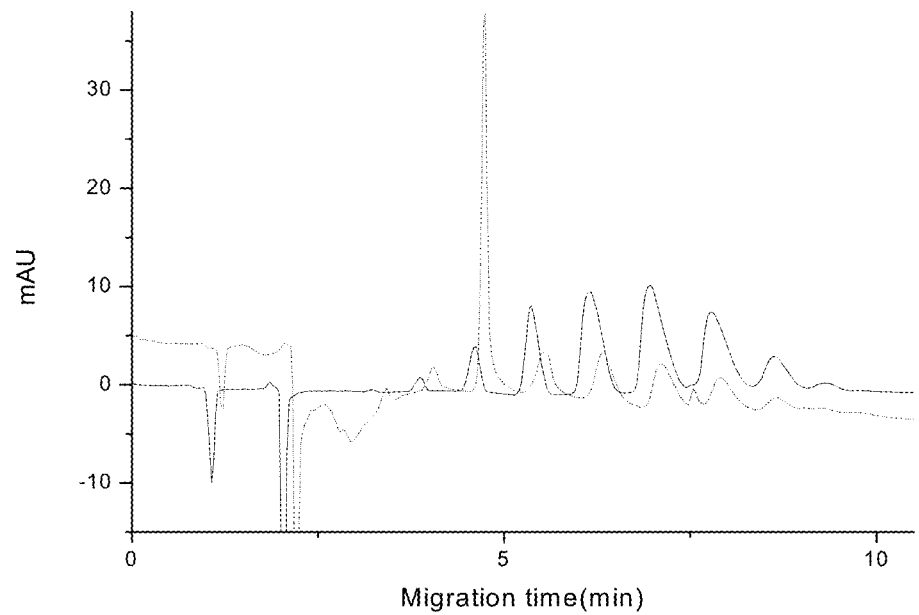
Figure: 10
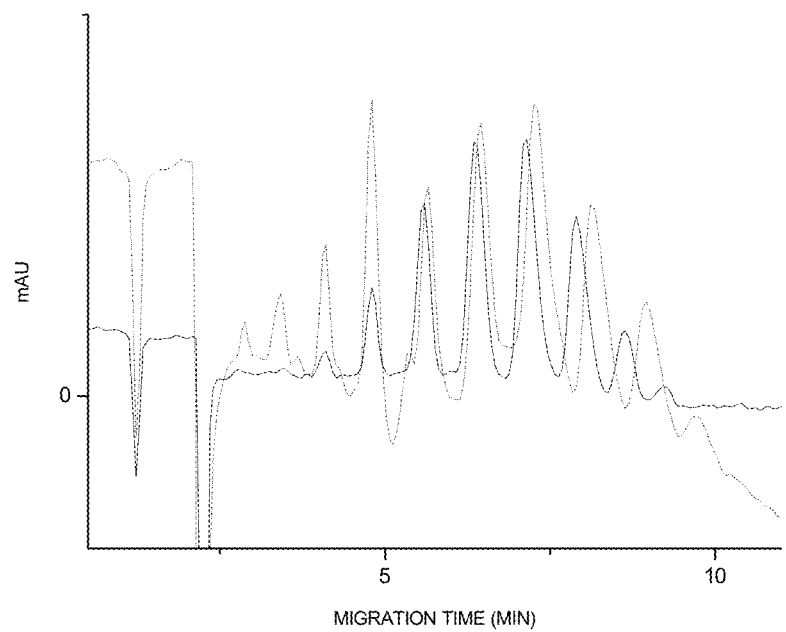

Figure: 11
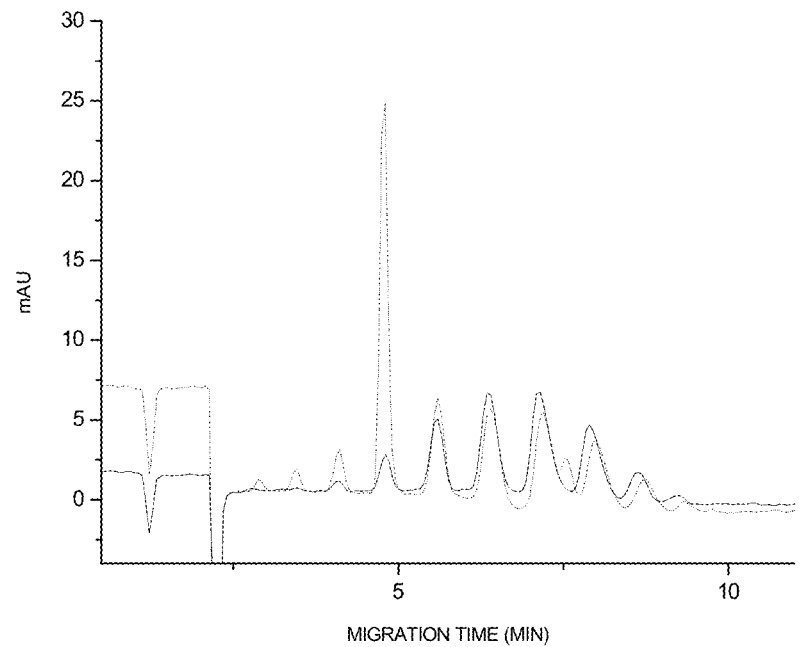
Figure: 12
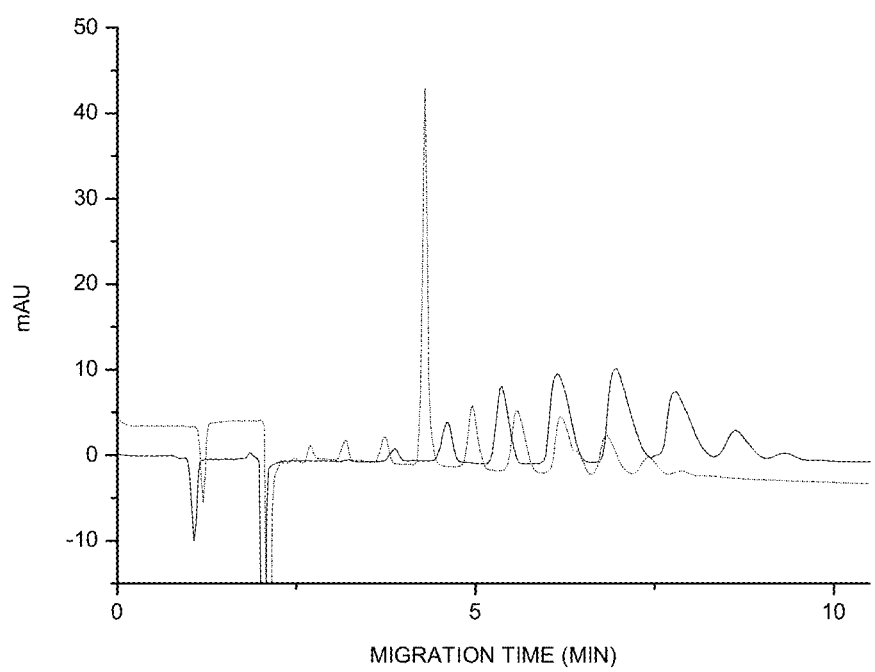

Figure: 13
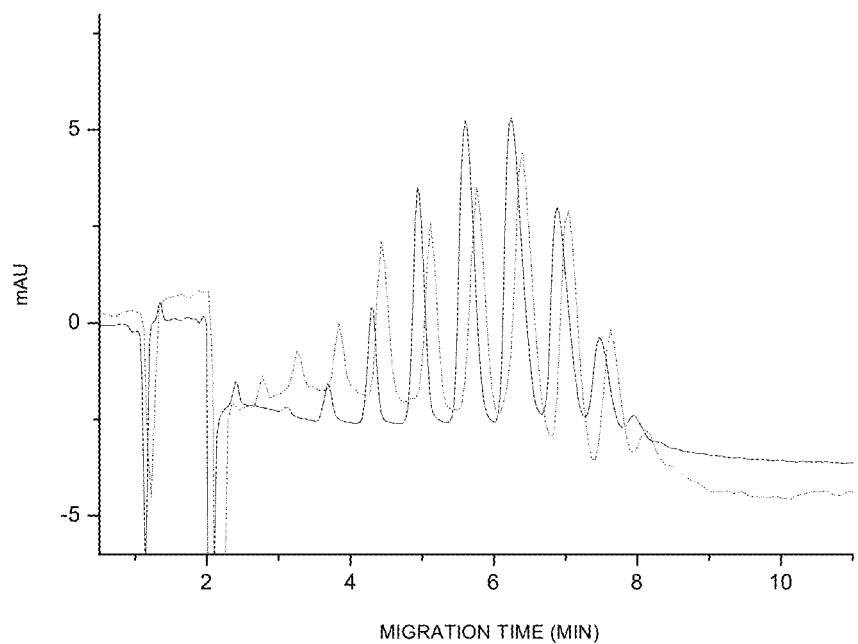
Figure: 14
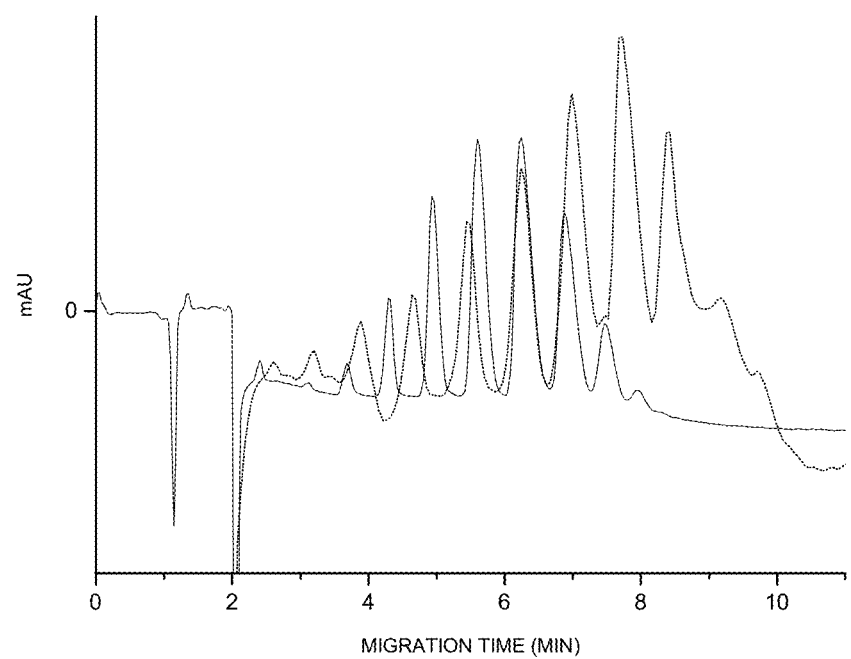

Figure: 15
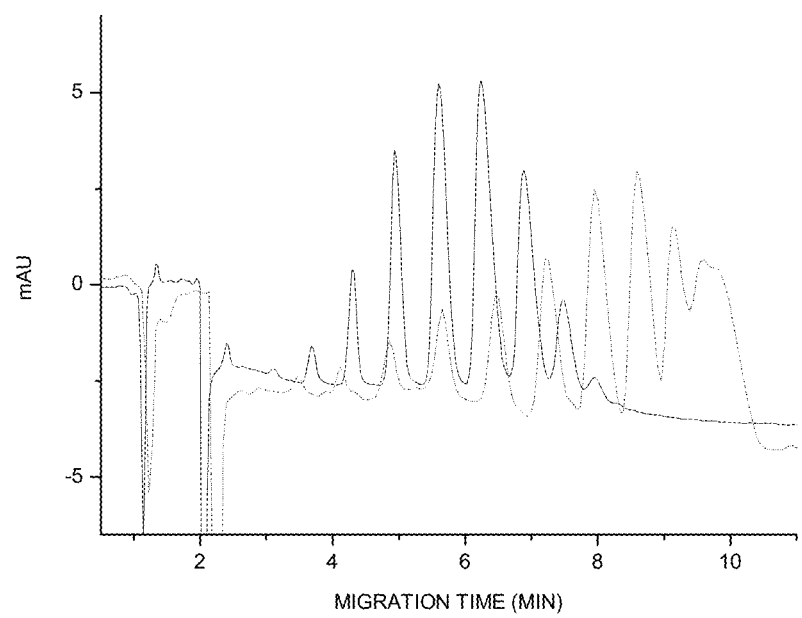
Figure: 16
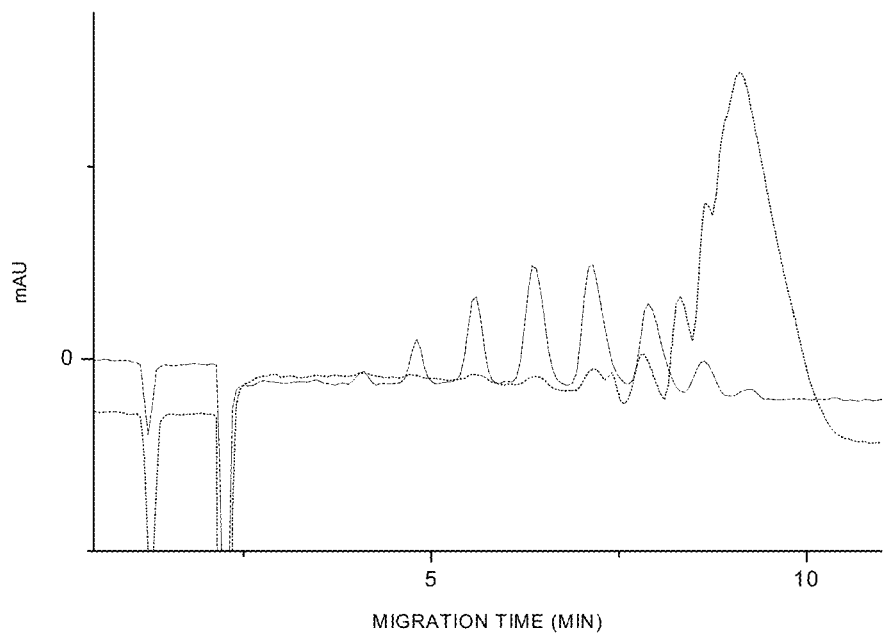

Figure: 17
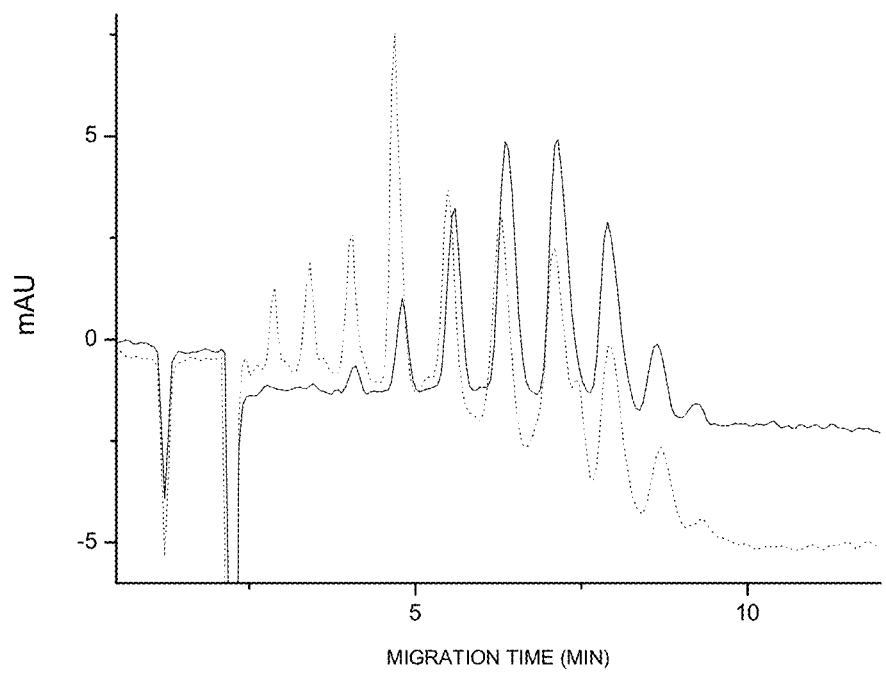
MIGRATION TIME (MIN)
Figure: 18
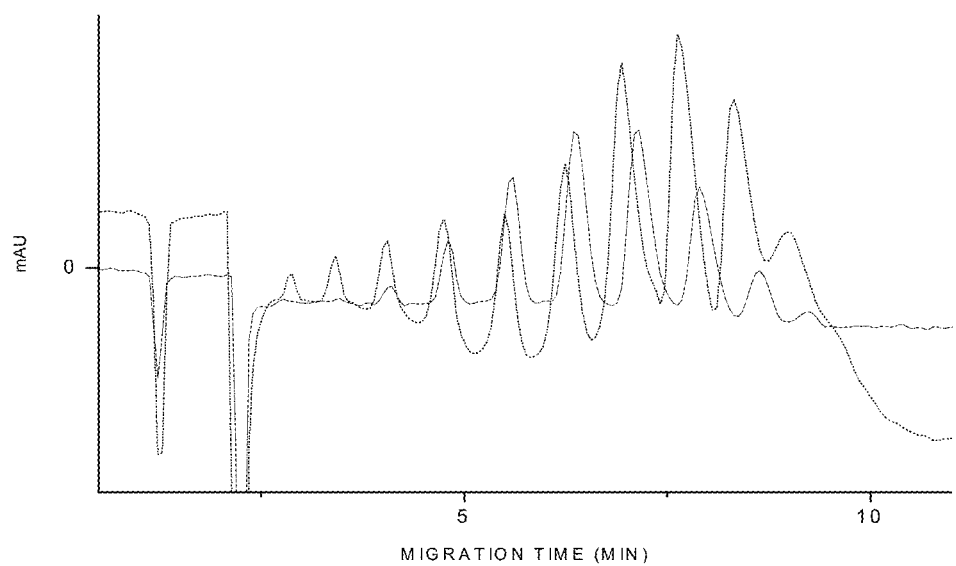
MIGRATION TIME (MIN)

Figure: 19
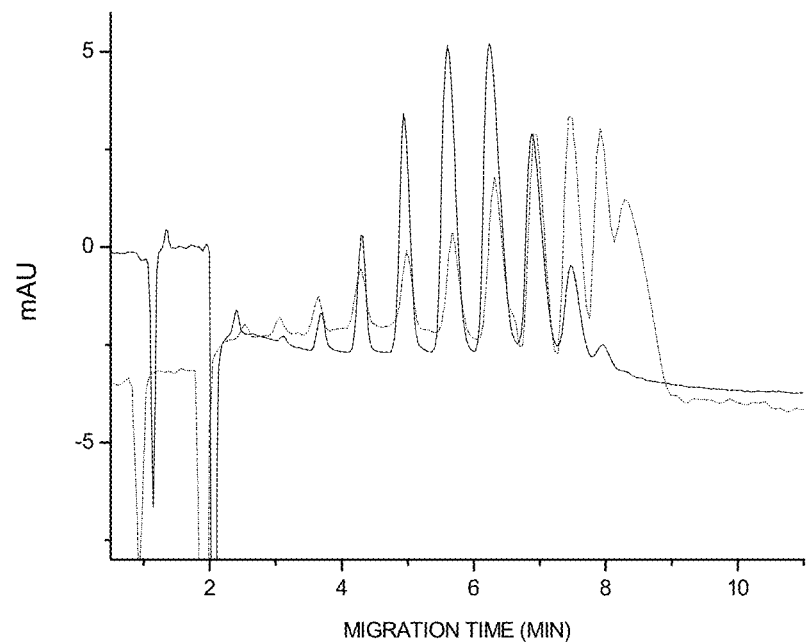
Figure: 20
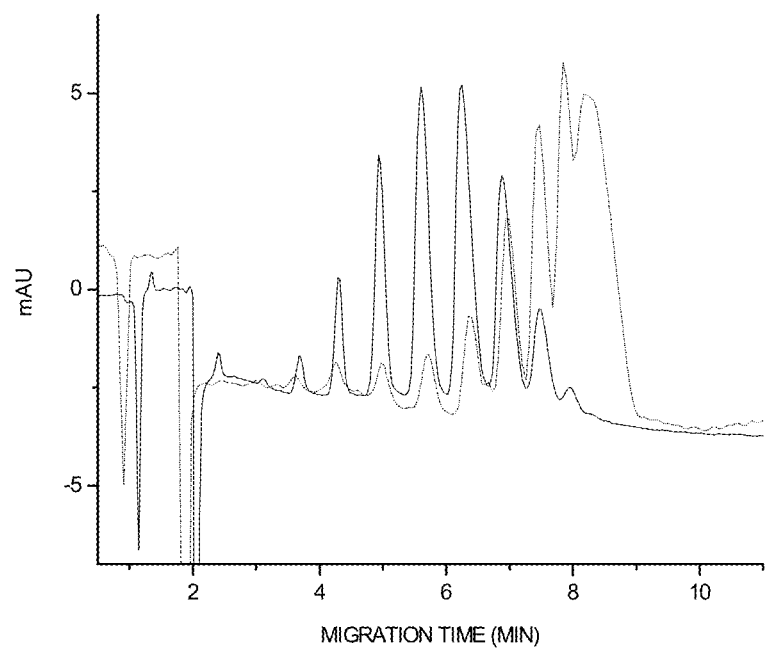

Figure: 22
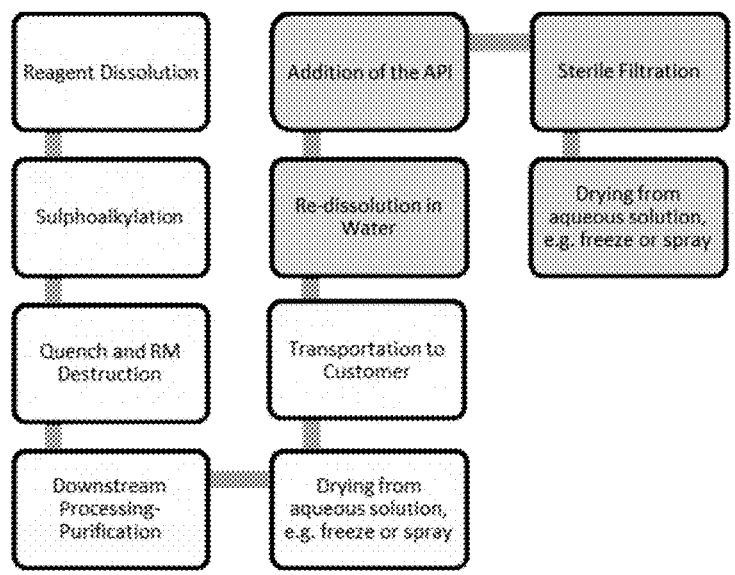
Figure: 23
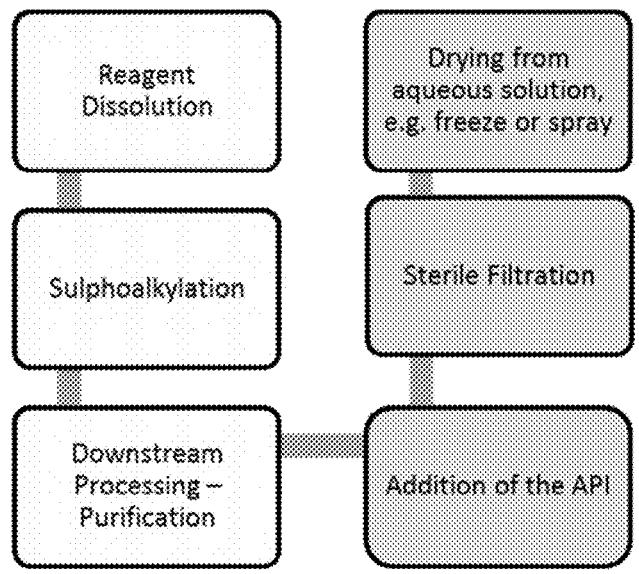

Figure: 24
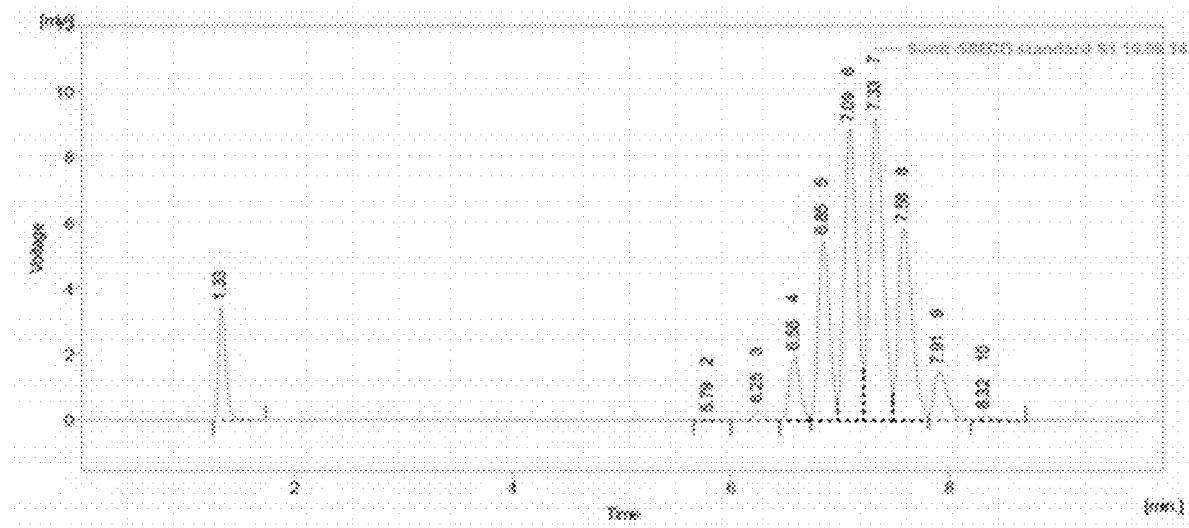
Figure: 25
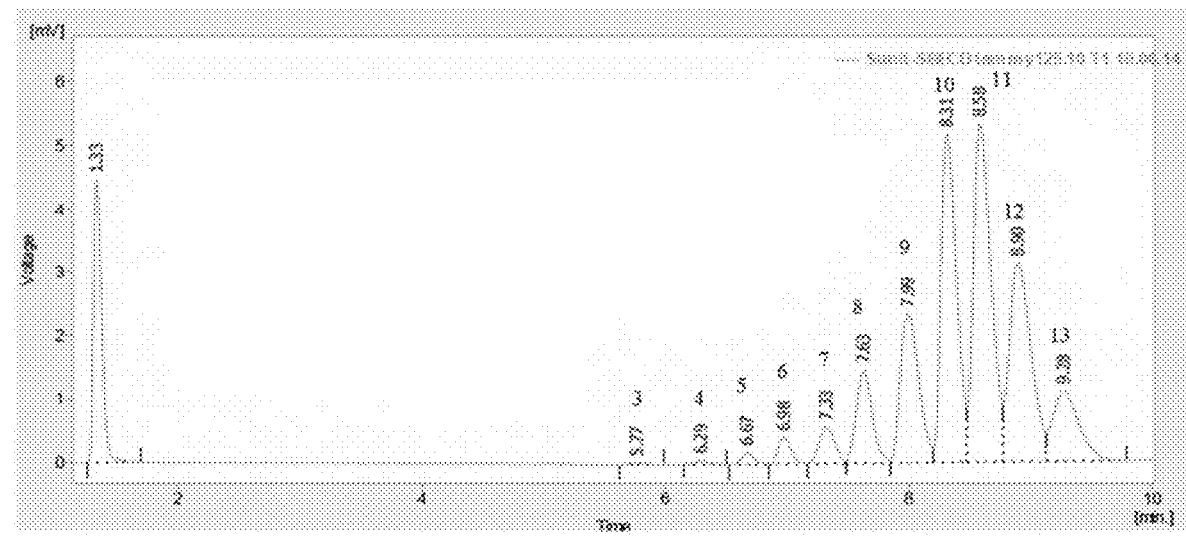

Figure: 26

| Butane sultone to β-cyclodextrin molar ratio | Sodium hydroxide to β-cyclodextrin molar ratio | Sodium hydroxide deficit/excess relative to US 5,376,645 (Stella) | Average Degree of Substitution | IDS$_n$ present in US 6,153,746 (Shah, 2000) and not in the CSTR produced SBECD | IDS$_n$ present in the CSTR produced SBECD and not in US 6,153,746 (Shah, 2000) | Corresponding figure number |
|---|---|---|---|---|---|---|
| 8:1 | 11:1 | | | | | 5 |
| 11:1 | 11:1 | | | | | 6 |
| 14:1 | 11:1 | | | | | 7 |
| 17:1 | 11:1 | | | | | 8 |
| 19:1 | 11:1 | | | | | 9 |
| 23:1 | 11:1 | | | | | 10 |
| 28:1 | 11:1 | | | | | 11 |
| 33:1 | 11:1 | | | | | 12 |
| 7:1 | 6:1 | -50% | 10.7 | None | IDS$_{11}$-IDS$_{14}$ | 13 |
| 7:1 | 9:1 | -25% | 6.9 | None | IDS$_1$, IDS$_{11}$ | 14 |
| 7:1 | 11:1 | 0% | 8.7 | None | IDS$_{11}$ – IDS$_{13}$ | 15 |
| 7:1 | 14:1 | +25% | 12.1 | IDS$_2$ – IDS$_6$ | IDS$_{11}$-IDS$_{14}$ | 16 |
| 10:1 | 6:1 | -50% | 6.0 | None | None | 17 |
| 10:1 | 9:1 | -25% | 6.8 | None | IDS$_1$, IDS$_{11}$ | 18 |
| 10:1 | 11:1 | 0% | 8.4 | None | IDS$_1$, IDS$_{11}$, IDS$_{12}$ | 19 |
| 10:1 | 14:1 | +25% | 10.4 | IDS$_2$ | IDS$_{11}$ – IDS$_{13}$ | 20 |

Figure: 27

| $IDS_n$ | USP-NF peak area percentage limit | $IDS_n$ present in US 6,153,746 (Shah, 2000) by HPLC | Acceptance | $IDS_n$ present in the CSTR 10:1 butane sultone:β-cyclodextrin molar ratio and a 6:1 Sodium hydroxide to β-cyclodextrin molar ratio | Acceptance |
|---|---|---|---|---|---|
| 1 | 0-0.3 | Not Detected | Accept | Not Detected | Accept |
| 2 | 0-0.9 | 0.13 | Accept | 2.71 | Reject |
| 3 | 0.5-5.0 | 0.88 | Accept | 5.49 | Reject |
| 4 | 2.0-10.0 | 4.91 | Accept | 12.48 | Reject |
| 5 | 10.0-20.0 | 14.61 | Accept | 19.01 | Accept |
| 6 | 15.0-25.0 | 25.45 | Reject | 19.61 | Accept |
| 7 | 20.0-30.0 | 29.50 | Accept | 17.57 | Reject |
| 8 | 10.0-25.0 | 19.01 | Accept | 14.39 | Accept |
| 9 | 2.0-12.0 | 4.99 | Accept | 7.06 | Accept |
| 10 | 0-4.0 | 0.51 | Accept | 1.70 | Accept |

Figure: 28
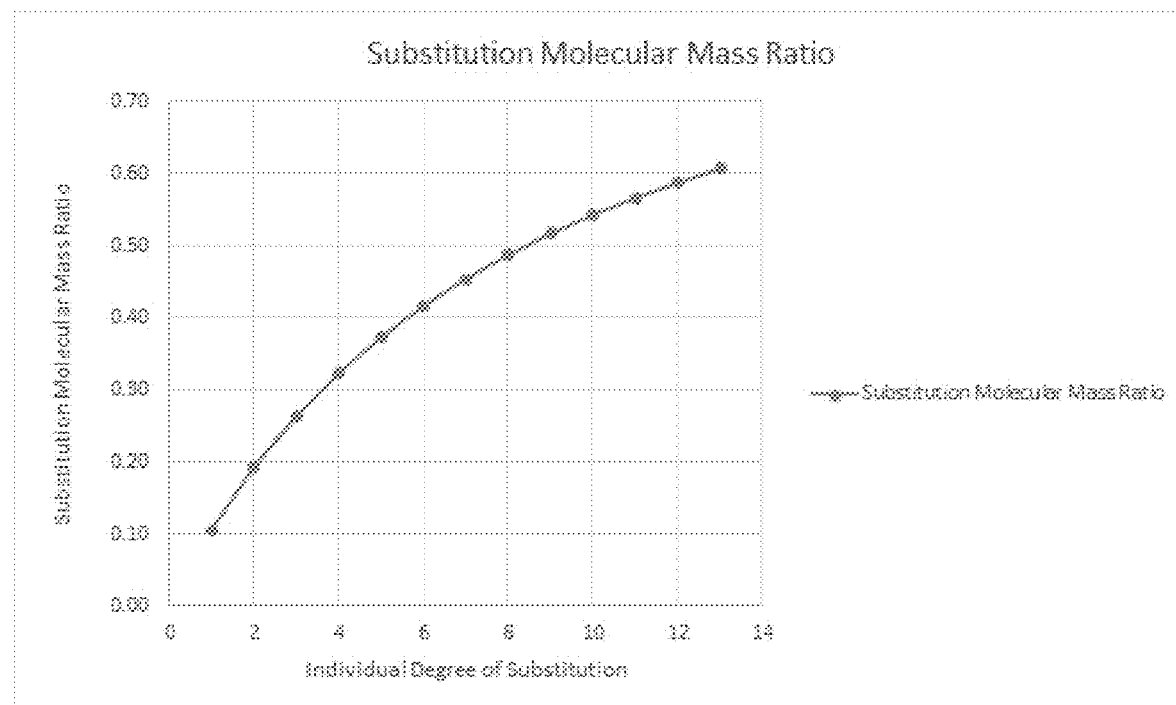
Figure: 29
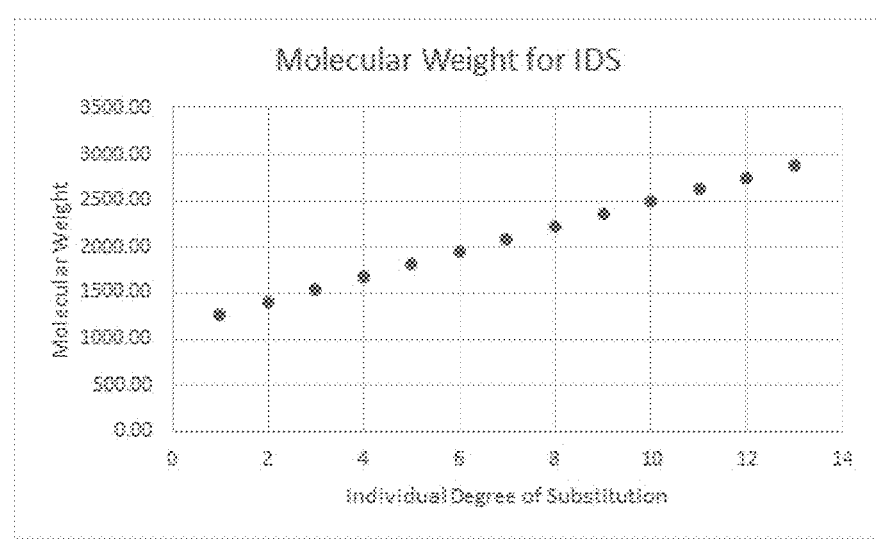

CYCLODEXTRIN

This patent application claims priority to, and the benefit of, U.S. Provisional Patent Application No. 61/847,509, filed Jul. 17, 2013, the entire contents of which are herein incorporated by reference in its entirety for all purposes.

The invention relates to cyclodextrins and derivatised cyclodextrins, such as sulphoalkyl ether β-cyclodextrin, and in particular to a novel method for the synthesis thereof. The invention is particularly concerned with producing sulphobutyl ether β-cyclodextrin. The invention extends to novel compositions comprising sulphoalkyl ether β-cyclodextrins, and to the uses of such compositions, for example as excipients in order to improve the solubility and chemical stability of drugs in solution.

Sulphobutyl ether β-cyclodextrin (SBE-β-CD or SBECD) is one of a class of polyanionic, hydrophilic water soluble cyclodextrin derivatives. The parent β-cyclodextrin can form an inclusion complex with certain active pharmaceutical ingredients (API) with two benefits, the apparent aqueous solubility of the API increases and, if labile functional groups are included, chemical stability is improved. However, the parent β-cyclodextrin suffers from two problems, including lower aqueous solubility and nephrotoxicity when given via injection, e.g. the intravenous route. Derivatisation of β-cyclodextrin (and its variants a and γ-cyclodextrin) has been shown to be beneficial with respect to both of these two defects. The first derivatised cyclodextrin was the hydroxypropyl derivative, which was later followed by sulphobutyl ether. These two derivatised cyclodextrins are the most commercially significant.

FIG. 1 illustrates the chemical reaction for the synthesis of SBE-β-CD from the reagents 3-cyclodextrin (β-CD) and 1, 4-butane sultone (BS). U.S. Pat. No. 6,153,746 (Shah et al, 2000) describes a batch synthesis of SBE-β-CD, the process being effectively divided into three main stages, i.e. initial reagent dissolution, a sulphoalkylation reaction and final reaction quenching. The reaction is then followed by downstream processing and purification, and ultimate isolation of the solid SBE-β-CD material. However, a problem associated with using a batch synthetic method is that a high proportion of lower substituted SBE-β-CD is observed. There is therefore a need to provide an improved synthetic method for producing substituted cyclodextrins, such as SBE-β-CD.

SBE-β-CD is currently used as an effective pharmaceutical excipient, and has been given the trade name Captisol®. To date, there are five US FDA-approved, SBE-β-CD-enabled drug products on the market: Nexterone (Baxter International); Geodon (Pfizer); Cerenia (Zoetis); Kyprolis (Onyx); Abilify (Bristol Myers Squibb).

In addition, as described in U.S. Pat. No. 6,632,803B1 (Harding, 2003), Pfizer has developed the clinically important antifungal drug, voriconazole, formulated with SBE-β-CD, as excipient. If Shah's and Harding's patents are considered together, the overall process to produce an injectable form of voriconazole follows a 10-step scheme, as shown in FIG. 22. Production of the SBE-β-CD excipient is represented by the six white boxes, and production of the final injectable voriconazole (i.e. formulation of the API with the excipient) is represented by the four grey boxes. The problems with this process are that it includes many steps, one of which is the transportation of the SBE-β-CD from the fine chemical manufacturing plant to the customer who adds the active ingredient, e.g. voriconazole. Furthermore, freeze drying and spray drying are expensive and time-consuming processes. There is therefore a need to provide an improved process for the production of pharmaceuticals comprising substituted cyclodextrin-based excipients.

As described in the Examples, the inventors carefully studied the batch SBE-β-CD production method that is described in U.S. Pat. No. 5,376,645 (Stella et al, 1994), and experimented with the stoichiometry of the reaction, and have devised a significantly improved continuous flow synthetic method for producing sulphoalkyl ether cyclodextrins, such as SBE-β-CD.

Hence, according to a first aspect of the invention, there is provided a method for preparing sulphoalkyl ether β-cyclodextrin, the method comprising contacting cyclodextrin with a base to form activated cyclodextrin, and separately contacting the activated cyclodextrin with an alkyl sultone to form sulphoalkyl ether β-cyclodextrin, characterised in that the sulphoalkylation reaction is carried out under continuous flow conditions.

In a second aspect, there is provided sulphoalkyl ether β-cyclodextrin obtained or obtainable by the method according to the first aspect.

The inventors have found that the continuous flow nature of the sulphoalkylation reaction in the method of the first aspect results in a surprisingly superior process compared to the prior art batch process, because it exhibits a greater reaction efficiency and results in a much tighter control of substitution of the resultant sulphoalkyl ether β-cyclodextrin, which is preferably sulphobutyl ether β-cyclodextrin (i.e. SBE-β-CD). Indeed, the continuous flow synthesis process of the invention substantially less than 50% of the amount of base (which is preferably sodium hydroxide) that is used in the prior art batch process, and only a 7:1 molar ratio of the alkyl sultone (which is preferably, 1, 4-butane sultone) to cyclodextrin instead of the 10:1 used by the prior art method. This finding was completely unexpected, since the inventors' expectation was that, at best, an equivalent synthetic efficiency between the batch and continuous flow methods would be seen. Accordingly, by using the continuous flow method of the first aspect, the alkyl sultone can react with the cyclodextrin more efficiently and completely to thereby generate higher degrees of substitution with more efficient use of the starting materials. It has also been noted that lower volumes of water are necessary to achieve chemical coupling.

In one embodiment of the method of the invention, the sulphoalkylation reaction is carried out under continuous flow conditions, whereas the activation reaction may be carried out either continuously, batch, or fed-batch. Preferably, however, the activation reaction is carried out as a batch process while the sulphoalkylation reaction is carried out under continuous flow conditions.

Problems associated with prior art methods which are fully batch, or fully continuous, (i.e. with respect to both the activation stage and the sulphoalkylation reaction stage) are that they result in the production of high concentrations of by-products (e.g. dimerisation products), produce SBE-β-CD with low average degrees of substitution, as well leave unreacted alkyl sultone.

Accordingly, the method of the invention, in which the activation stage is batch and the sulphoalkylation reaction stage is continuous, results in lower concentrations of by-products, SBE-β-CD with a higher average degree of substitution, and also most if not all of the alkyl sultone is reacted.

Preferably, the cyclodextrin is α-, β- or γ-cyclodextrin. It will be appreciated that α- and γ-cyclodextrin can be used as pharmaceutical excipients for instance in commercially available drugs such as Prostavasin, Opalamon (β-CD) and Voltaren (modified γ-CD). Most preferably, however, the cyclodextrin is β-cyclodextrin.

The alkyl sultone may comprise propane sultone. Thus, sulphoalkyl ether β-cyclodextrin preferably comprises sulphopropyl ether β-cyclodextrin (SPE-β-CD).

However, most preferably the alkyl sultone comprises 1, 4-butane sultone. Preferably, therefore, the sulphoalkyl ether β-cyclodextrin comprises sulphobutyl ether β-cyclodextrin (SBE-β-CD).

The resultant substituted sulphoalkyl ether β-cyclodextrin according to the second aspect is novel per se because it exhibits a higher average degree of substitution, for a lower input of alkyl sultone and base than that which is produced using the known batch process. The batch method of preparing substituted sulphoalkyl ether β-cyclodextrin produces a higher concentration of lower degrees of sulphoalkyl ether β-cyclodextrin substitution than that produced using continuous flow. As shown in FIGS. 20 and 25, the continuous flow process of the invention however results in a lower concentration of lower substituted sulphoalkyl ether β-cyclodextrin (i.e. a degree of substitution value of 1-4) and surprisingly much higher concentrations of the higher substituted sulphoalkyl ether β-cyclodextrin (i.e. individual degrees of substitution values of 4-13).

Thus, preferably the average degree of substitution (ADS) of the sulphoalkyl ether β-cyclodextrin produced by the method of the first aspect or the SBE-β-CD of the second aspect is greater than 7, more preferably 7.3 or more, more preferably 8 or more, even more preferably 9 or more, and most preferably to or more. The skilled person will appreciate that it is possible to calculate the substitution degree (i.e. the substitution envelope) by using the following Formula:

$$ADS=\Sigma((PAC) \times (MT)/SCA \times 100)/100$$

where PAC refers to the peak area count; MT refers to the migration time; and SCA refers to the summation of corrected area. The inventors believe that this increased ADS is an important feature of the invention.

Thus, in a third aspect there is provided a composition comprising sulphobutyl ether β-cyclodextrin (SBE-β-CD), wherein the average degree of substitution (ADS) is 7 or more, preferably 7.3 or more, preferably 8 or more, even more preferably 9 or more, and most preferably to or more.

Since the batch method produces a higher proportion of lower substituted SBE-β-CD than higher substituted SBE-β-CD, the continuous flow method of the invention provides a significant advantage.

Preferably, the composition of the third aspect comprises SBE-β-CD having a Substitution Molecular Mass Fraction (SMF) greater than 0.57, more preferably greater than 0.58, and even more preferably greater than 0.59. Preferably, the composition of the third aspect comprises SBE-β-CD having an SMF greater than 0.60, and more preferably greater than 0.61. Example 8 describes how the SMF value can be calculated with reference to FIG. 28.

The base may be an alkali metal hydroxide, for example sodium hydroxide, lithium hydroxide or potassium hydroxide. It is preferred that the base comprises sodium hydroxide.

The molar ratio of base (which is preferably sodium hydroxide) to cyclodextrin is preferably within the range of 2:1 to 22:1, preferably 6:1 to 20:1, more preferably 6:1 to 15:1, and even more preferably 6:1 to 14:1. The preferred molar ratio of base to cyclodextrin is 6:1 to 14:1. The most preferred molar ratio of base to cyclodextrin is 6:1 to 15:1.

During their research, the inventors carefully considered the prior art batch process, and found that the base, employed to chemically activate the β-cyclodextrin hydroxyl groups, has a tendency to attack the alkyl sultone reagent, thereby reducing its effective concentration, and, as a result, reduces the average degree of substitution in the final product with the generation of low degree of substitution species. Accordingly, during the method of the first aspect, it is preferred that the base is kept separate from the alkyl sultone, preferably 1, 4-butane sultone. Preferably, the base is first separately reacted with the cyclodextrin in order to produce the activated cyclodextrin. This reaction is preferably conducted in a first reservoir vessel. The activation reaction may therefore be carried out as a batch or fed-batch process. Preferably, the base and cyclodextrin form an aqueous solution. The activation reaction is preferably conducted at a temperature of about 50 to 95° C., more preferably 60 to 70° C. The activation reaction is preferably conducted at atmospheric pressure.

Preferably, the alkyl sultone is contained within a second reservoir vessel. Preferably, the first and second vessels are not directly connected to each other, such that the sultone and the base do not react with each other.

The activated cyclodextrin (i.e. aqueous solution) and the alkyl sultone (i.e. pure) are preferably fed to a confluent 3-way junction where they are allowed to react to produce the substituted sulphoalkyl ether β-cyclodextrin. The activated aqueous cyclodextrin and the alkyl sultone are preferably pumped at a controlled rate to the junction.

The molar ratio of sultone (preferably 1, 4-butane sultone) to cyclodextrin (preferably β-cyclodextrin) is preferably between about 7:1 and 33:1. Preferably, the molar ratio of sultone to cyclodextrin is 7:1 to 17:1.

The sulphoalkylation reaction is preferably conducted at a temperature of 60 to 100° C., more preferably 65 to 95° C., and even more preferably 60 to 70° C. The sulphoalkylation reaction is preferably conducted at atmospheric pressure.

The alkylation reaction may be carried out in a continuous stirred tank reactor (CSTR) or a flow reactor with efficient mixing and of suitable length to allow the reaction to complete within the reactor tubing. The activation of β-cyclodextrin is an important process parameter prior to reaction and this must continue irrespective of the reactor architecture.

In a preferred embodiment, the method of the invention comprises contacting the cyclodextrin in a batch or fed-batch reaction with the base to form activated cyclodextrin, and separately contacting the activated cyclodextrin with an alkyl sultone to form sulphoalkyl ether β-cyclodextrin, wherein the sulphoalkylation reaction is carried out under continuous flow conditions.

In a most preferred embodiment, therefore, the method comprises separately reacting β-cyclodextrin with sodium hydroxide in a batch or fed-batch reaction to form activated β-cyclodextrin, and then separately contacting the activated β-cyclodextrin with 1, 4-butane sultone to form SBE-β-CD under continuous flow conditions.

The inventors have surprisingly demonstrated that it is possible to accurately control and manipulate the average degree of substitution (ADS) of sulphoalkyl ether β-cyclodextrin produced in sulphoalkylation reaction by varying the sodium hydroxide concentration in the initial activation reaction.

Preferably, therefore, the method comprises controlling the average degree of substitution (ADS) of sulphoalkyl ether β-cyclodextrin in the sulphoalkylation reaction by varying the base concentration in the initial activation reaction. This is an important feature of the invention.

Accordingly, in another aspect, there is provided use of sodium hydroxide concentration for controlling the average degree of substitution (ADS) of sulphoalkyl ether β-cyclodextrin produced in a sulphoalkylation reaction between activated cyclodextrin and an alkyl sultone.

Preferably, the use comprises carrying out an initial activation reaction between cyclodextrin and the base to form activated cyclodextrin.

To date, no one has appreciated that the concentration of sodium hydroxide can be varied in the initial activation reaction in order to control and manipulate the average degree of substitution (ADS) of resultant sulphoalkyl ether β-cyclodextrin.

The unsubstituted parent β-CD is shown to induce irreversible nephrotic damage to the kidney cells when used as an excipient in injection formulations. SBE-β-CD causes reversible vacuolation of renal cells but not nephrotic damage and is therefore preferred for use in injectable formulations. Given that the inventors have clearly demonstrated that the method of the invention results in a lower concentration of low degree of substitution SBE-β-CD species it is believed that the SBE-β-CD may cause lower levels of physiological changes to renal cells. Accordingly, they believe that the SBE-β-CD of the second aspect or the composition of the third aspect can be used to reduce changes in renal cells when used as a drug delivery system.

Hence, in a fourth aspect there is provided the use of sulphoalkyl ether β-cyclodextrin of the second aspect, or the composition of the third aspect, as a drug delivery system.

Preferably, the drug delivery system is an excipient, which preferably exhibits little or no side effects with regard to renal physiology. Preferably, the sulphoalkyl ether β-cyclodextrin comprises sulphobutyl ether β-cyclodextrin (SBE-β-CD).

In a fifth aspect, therefore, there is provided a pharmaceutical excipient comprising the sulphoalkyl ether β-cyclodextrin of the second aspect, or the composition of the third aspect.

Preferably, therefore, the sulphoalkyl ether-β-cyclodextrin comprises sulphobutyl ether β-cyclodextrin (SBE-β-CD).

Advantageously, as described in examples, use of the continuous flow method of invention means that it is now possible to combine the two processes shown in FIG. 22 (i.e. excipient production, and pharmaceutical production), to result in the 6-step process chain shown in FIG. 23.

Hence, in a sixth aspect, there is provided a method of preparing a pharmaceutical composition, the method comprising preparing the pharmaceutical excipient according to the fifth aspect, and contacting the excipient with an active pharmaceutical ingredient (API) to produce a pharmaceutical composition.

In contrast to the process shown in FIG. 22, the production of the sulphobutyl ether cyclodextrin, acting as excipient, is now represented in FIG. 23 by just three white boxes (instead of six), and formulation of the API with the excipient to create the pharmaceutical product is represented by only three grey boxes (instead of four). Accordingly, the method of the invention means that three of the steps shown in FIG. 22 can be omitted. Therefore, it is now unnecessary to transport the sulphobutyl ether cyclodextrin from the fine chemical manufacturer to the customer. This would also include warehousing, etc. Secondly, the sulphoalkyl ether β-cyclodextrin can be manufactured on a just-in-time, just-enough basis. Thirdly, one of the two expensive and time-consuming freeze or spray drying process steps can be avoided.

Preferably, the method comprises contacting the excipient with an active pharmaceutical ingredient (API) to produce a pharmaceutical composition without drying or isolating the excipient.

Preferably, the pharmaceutical excipient comprises sulphobutyl ether β-cyclodextrin.

Preferably, the active pharmaceutical ingredient comprises voriconazole, ziprasidone, aripiprazole, maropitant, amiodarone, or carfilzomib, or their salts, solvates, polymorphs, pseudopolymorphs or co-crystals.

In another embodiment, the method of the invention comprises separately reacting β-cyclodextrin with sodium hydroxide to form activated β-cyclodextrin, and then separately contacting the activated β-cyclodextrin with 1, 4-butane sultone to form SBE-β-CD, all under continuous flow conditions. Advantageously, the stoichiometry of the reaction can be readily controlled by varying the flow rates of the activated cyclodextrin solution and/or liquid sultone.

Hence, in another aspect of the invention, there is provided a method for preparing sulphoalkyl ether β-cyclodextrin, the method comprising contacting cyclodextrin with a base to form activated cyclodextrin, and separately contacting the activated cyclodextrin with an alkyl sultone to form sulphoalkyl ether β-cyclodextrin, characterised in that the process is carried out under continuous flow conditions.

All of the features described herein (including accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying drawings, in which:—

FIG. 1 shows the chemical reaction for the synthesis of sulphobutyl ether β-cyclodextrin (SBE-β-CD) from β-cyclodextrin (CD) and 1, 4-butane sultone (BS);

FIG. 2 is a schematic representation for an embodiment of an apparatus for carrying out continuous flow (CF) synthesis for SBE-β-CD according to the invention;

Figure 4:
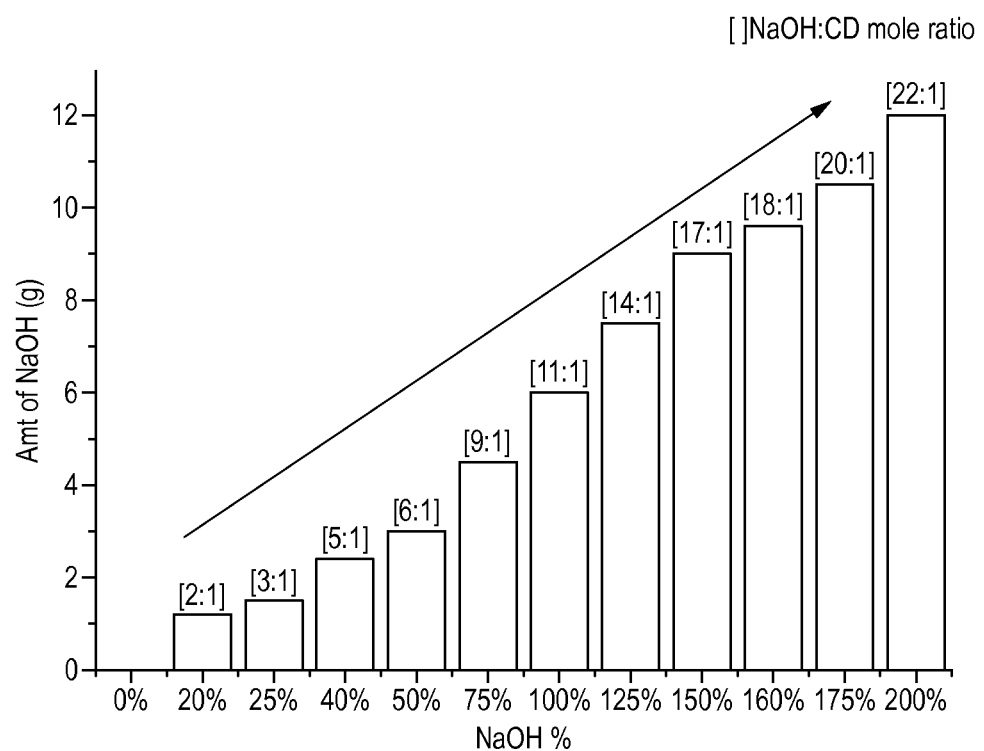

FIG. 4 is a graph showing the changing amount of NaOH at 7:1 and 10:1 BS/CD mole ratio; 100% nominal sodium hydroxide is equivalent to the base content used in U.S. Pat. No. 5,376,645 (Stella et al, 1994)

FIG. 5 shows electropherograms of batch manufactured SBE-β-CD (U.S. Pat. No. 6,153,746-Shah et al, 2000) as the solid line and SBE-β-CD manufactured by a continuous flow process according to the invention, with a 8:1 butane sultone to β-cyclodextrin molar ratio as the dotted line. The sodium hydroxide to β-CD molar ratio is 11:1.

FIG. 6 shows electropherograms of batch manufactured SBE-β-CD (U.S. Pat. No. 6,153,746-Shah et al, 2000) as the solid line and SBE-β-CD manufactured by a continuous flow process according to the invention, with a 11:1 butane sultone to β-cyclodextrin molar ratio as the dotted line. The sodium hydroxide to β-CD molar ratio is 11:1.

FIG. 7 shows electropherograms of batch manufactured SBE-β-CD (U.S. Pat. No. 6,153,746-Shah et al, 2000) as the solid line and SBE-β-CD manufactured by a continuous flow process according to the invention, with a 14:1 butane sultone to β-cyclodextrin molar ratio as the dotted line. The sodium hydroxide to β-CD molar ratio is 11:1.

FIG. 8 shows electropherograms of batch manufactured SBE-β-CD (U.S. Pat. No. 6,153,746-Shah et al, 2000) as the solid line and SBE-β-CD manufactured by a continuous flow process according to the invention, with a 17:1 butane sultone to β-cyclodextrin molar ratio as the dotted line. The sodium hydroxide to β-CD molar ratio is 11:1.

FIG. 9 shows electropherograms of batch manufactured SBE-β-CD (U.S. Pat. No. 6,153,746-Shah et al, 2000) as the solid line and SBE-β-CD manufactured by a continuous flow process according to the invention, with a 19:1 butane sultone to β-cyclodextrin molar ratio as the dotted line. The sodium hydroxide to β-CD molar ratio is 11:1.

FIG. 10 shows electropherograms of batch manufactured SBE-β-CD (U.S. Pat. No. 6,153,746-Shah et al, 2000) as the solid line and SBE-β-CD manufactured by a continuous flow process according to the invention, with a 23:1 butane sultone to β-cyclodextrin molar ratio as the dotted line. The sodium hydroxide to β-CD molar ratio is 11:1.

FIG. 11 shows electropherograms of batch manufactured SBE-β-CD (U.S. Pat. No. 6,153,746-Shah et al, 2000) as the solid line and SBE-β-CD manufactured by a continuous flow process according to the invention, with a 28:1 butane sultone to β-cyclodextrin molar ratio as the dotted line. The sodium hydroxide to β-CD molar ratio is 11:1.

FIG. 12 shows electropherograms of batch manufactured SBE-β-CD (U.S. Pat. No. 6,153,746-Shah et al, 2000) as the solid line and SBE-β-CD manufactured by a continuous flow process according to the invention, with a 33:1 butane sultone to β-cyclodextrin molar ratio as the dotted line. The sodium hydroxide to β-CD molar ratio is 11:1.

FIG. 13 shows electropherograms of batch manufactured SBE-β-CD (U.S. Pat. No. 6,153,746-Shah et al, 2000) as the solid line and SBE-β-CD manufactured by a continuous flow process according to the invention, with a 7:1 butane sultone to β-cyclodextrin molar ratio as the dotted line. The sodium hydroxide to β-CD molar ratio is 6:1.

FIG. 14 shows electropherograms of batch manufactured SBE-β-CD (U.S. Pat. No. 6,153,746-Shah et al, 2000) as the solid line and SBE-β-CD manufactured by a continuous flow process according to the invention, with a 7:1 butane sultone to β-cyclodextrin molar ratio as the dotted line. The sodium hydroxide to β-CD molar ratio is 9:1.

FIG. 15 shows electropherograms of batch manufactured SBE-β-CD (U.S. Pat. No. 6,153,746-Shah et al, 2000) as the solid line and SBE-β-CD manufactured by a continuous flow process according to the invention, with a 7:1 butane sultone to β-cyclodextrin molar ratio as the dotted line. The sodium hydroxide to β-CD molar ratio is 11:1.

FIG. 16 shows electropherograms of batch manufactured SBE-β-CD (U.S. Pat. No. 6,153,746-Shah et al, 2000) as the solid line and SBE-β-CD manufactured by a continuous flow process according to the invention, with a 7:1 butane sultone to β-cyclodextrin molar ratio as the dotted line. The sodium hydroxide to β-CD molar ratio is 14:1.

FIG. 17 shows electropherograms of batch manufactured SBE-β-CD (U.S. Pat. No. 6,153,746-Shah et al, 2000) as the solid line and SBE-β-CD manufactured by a continuous flow process according to the invention, with a 10:1 butane sultone to β-cyclodextrin molar ratio as the dotted line. The sodium hydroxide to β-CD molar ratio is 6:1.

FIG. 18 shows electropherograms of batch manufactured SBE-β-CD (U.S. Pat. No. 6,153,746-Shah et al, 2000) as the solid line and SBE-β-CD manufactured by a continuous flow process according to the invention, with a 10:1 butane sultone to β-cyclodextrin molar ratio as the dotted line. The sodium hydroxide to β-CD molar ratio is 9:1.

FIG. 19 shows electropherograms of batch manufactured SBE-β-CD (U.S. Pat. No. 6,153,746-Shah et al, 2000) as the solid line and SBE-β-CD manufactured by a continuous flow process according to the invention, with a 10:1 butane sultone to β-cyclodextrin molar ratio as the dotted line. The sodium hydroxide to β-CD molar ratio is 11:1.

FIG. 20 shows electropherograms of batch manufactured SBE-β-CD (U.S. Pat. No. 6,153,746-Shah, et al 2000) as the solid line and SBE-β-CD manufactured by a continuous flow process according to the invention, with a 10:1 butane sultone to β-cyclodextrin molar ratio as the dotted line. The sodium hydroxide to β-CD molar ratio is 14:1.

Figure 21:
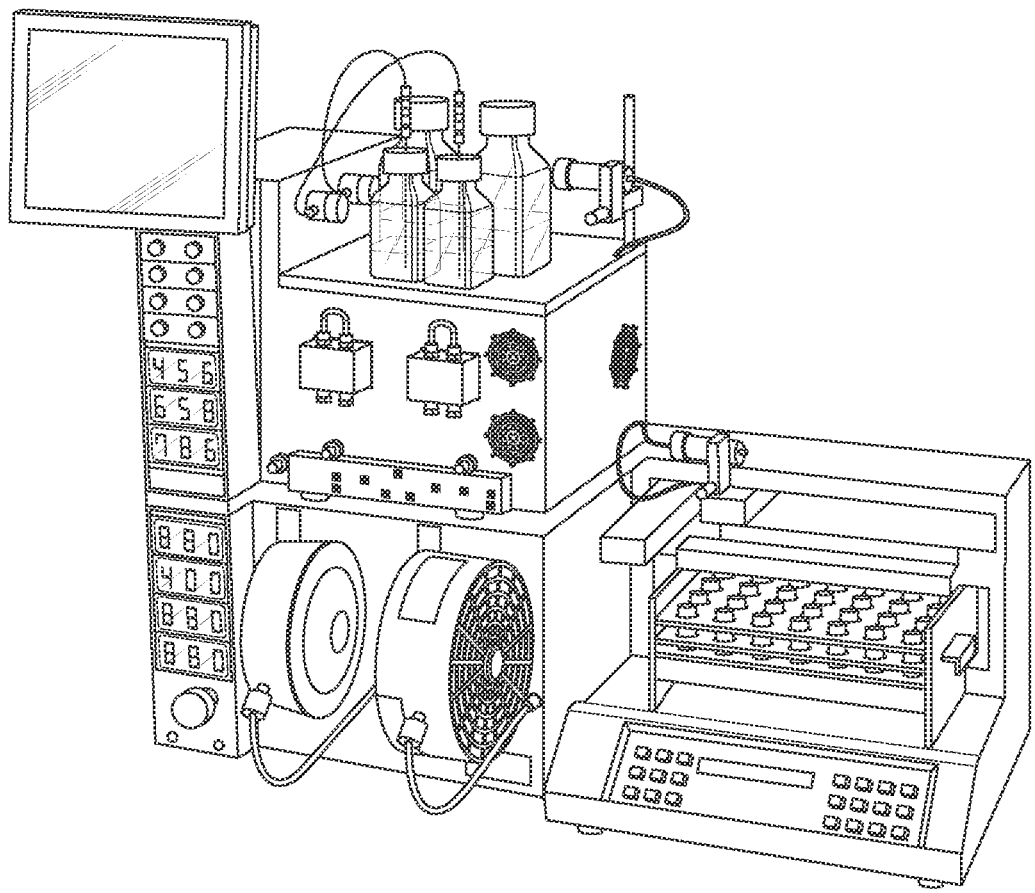

FIG. 21 shows a Vapourtec integrated flow reactor and associated equipment that will ultimately be preferred for the integrated manufacture of the SBE-β-CD and API in a secondary pharmaceutical production manufacturing area to produce the drug product.

FIG. 22 is a schematic representation of a conventional process chain for voriconazole Injection Based on the standard SBECD batch process and Fine Chemical Model (excipient production in white; secondary pharmaceutical production in grey).

FIG. 23 is a schematic representation of a revised process chain for voriconazole Injection Based on an SBECD continuous flow (CF) process and Integrated Manufacture Model (excipient production in white; secondary pharmaceutical production in grey).

FIG. 24 is a chromatogram of sulphobutylether β-cyclodextrin produced by the method described in U.S. Pat. No. 6,153,746 (Shah, 2000), and tested according to the methods described in United States Pharmacopoeia 35/National Formulary 30 (USP35/NF30). HPLC conditions are based on a gradient separation with a CD-Screen-DAP column and ELSD detection.

FIG. 25 is a chromatogram of sulphobutylether β-cyclodextrin produced by the method according to the invention. Reaction conditions correspond to those used to generate FIG. 20, and HPLC conditions are based on a gradient separation with a CD-Screen-DAP column and ELSD detection.

FIG. 26 is a table showing shows a summary of the data adding the Average Degree of Substitution data and dispersion data.

FIG. 27 is a table describing an attempt to produce material compliant with the USP35/NF30 monograph with the use of more moderate reaction conditions.

FIG. 28 is a graph showing substitution molecular mass ratio for SBE-β-CD.

FIG. 29 is a graph showing the molecular weight and individual degree of substitution for SBE-β-CD.

EXAMPLE

The inventors have developed a novel continuous flow (CF) method for the synthesis of sulphoalkyl ether-β-cyclodextrin, for example sulphobutyl ether β-cyclodextrin (SBE-β-CD). The invention includes novel compositions comprising sulphoalkyl ether β-cyclodextrins, and to therapeutic uses of such compositions, for example to improve the solubility and chemical stability of drugs in solution.

Materials

Beta cyclodextrin (β-CD), 1, 4-Butane Sultone (BS), Water for injections and sodium hydroxide (NaOH).

Laboratory Equipment

Continuous stirred tank reactor (CSTR) vessel, Masterflex pump, Hotplate stirrer, Water bath, PTFE tubing (2 mm ID/4 mm ID), Omnifit Connectors, Dialysis tubing (Biotech grade, Cellulose Ester, 0.5-1 kDa MWCO).

Methods

The set-up for the continuous flow experiments consisted of two Masterflex pumps (8, 10) connected to a double 10 ml (i.e. two 10 ml chambers) jacketed continuous stirred tank reactor (CSTR) or holding chamber (14) used as a holding chamber/sight glass. The two pumps (8, 10) were connected to the CSTR/holding chamber (14) via a three-way connector (12) and PTFE tubing. Non-return valves were fitted in line in the vicinity of the three-way connector (12) to prevent the reagent stream reverse flow as a result of differential flow pressure in either of the feed lines. In one embodiment, the PTFE tubing was put in a water bath to maintain temperature at approximately 50-60° C. In another embodiment, the PTFE tubing was put in a water bath to maintain temperature at approximately 60-100° C.

In a round bottom flask, a stock solution of β-CD in NaOH solution (4) was first prepared as follows: 15 g of β-CD ($1.32 \times 10^{-2}$ mole) was added with stirring to an aqueous solution composed of 6 g of NaOH in 30 ml water. This solution was maintained between 60-70° C. with a hotplate stirrer.

At the given drive speeds, pump (8) was used to deliver stock β-CD solution into the CSTR (14) via a three way connector (12) where the reaction initially takes place, while pump (10) was used to also deliver neat butane sultone (6), at ambient temperature, through the connector (12) into the CSTR (14). However, in some embodiments, the neat sultone (6) can be heated to 60-90° C. The CSTR (14) contained two 10 ml chambers and was provided to increase the residence time for the reaction to continue, having started in the connector (12). In one embodiment, pump (8) was first turned on to feed the β-CD until it reached the first chamber of the CSTR (14), after which pump (10) was then turned on to feed the butane sultone into the CSTR (14). However, in another embodiment, pumps (8, 10) are both activated at the same time in order to avoid pumping pure β-CD through the system to produce higher than desirable unreacted precursor that would ultimately need to be removed by downstream processing. An internal vortex circulation was generated within the continuous flowing reaction stream within the CSTR (14), which ensured rapid mixing. Efficient stirring appears to be very important to the success of the process. The reaction solution was delivered via pumps (8, 10) into the CSTR (14) in a continuous manner.

The PTFE tubing is about 30 cm in length and is not sufficient for the reaction to complete prior to entry into the CSTR (14). As two phases are seen in the first chamber of the CSTR (14), it is most likely that small volumes of the heated reagents are delivered and react there. Provided that the flow rate is not excessively high, the second chamber of the CSTR (14) and the receiving vessel both contain clear liquid suggesting that the reaction is complete upon exit from the first chamber of the CSTR (14). High flow rates will deliver unreacted material to the second chamber and, in extreme circumstances, to the receiving vessel. The crude product was harvested in a 20 ml sample bottle.

Continuous flow experiments were carried out at different drive speed combinations for pump (8) and (10) thus obtaining a series of BS:CD mole ratio, as shown in Tables 1 and 2.

TABLE 1

The relationship between pump drive speed and flow rate giving rise to different butane sultone-β-cyclodextrin molar ratios - constant β-cyclodextrin flow rate.

| | Butane sultone | | | | | | | | β- CD |
|---|---|---|---|---|---|---|---|---|---|
| Drive speed(rpm) | 3 | 4 | 5 | 6 | 7 | 8 | 10 | 12 | 8 |
| Flow rate(ml/min) | 0.27 | 0.36 | 0.45 | 0.54 | 0.63 | 0.72 | 0.90 | 1.08 | 0.72 |
| Concentration Mol/min | $2.65e^{-3}$ | $3.53e^{-3}$ | $4.41e^{-3}$ | $5.29e^{-3}$ | $6.17e^{-3}$ | $7.04e^{-3}$ | $8.82e^{-3}$ | $1.06e^{-2}$ | $3.17e^{-3}$ |
| Molar ratio [BS:β-CD] | 8:1 | 11:1 | 14:1 | 17:1 | 19:1 | 23:1 | 28:1 | 33:1 | — |

TABLE 2

The relationship between pump drive speed and flow rate giving rise to different butane sultone-β-cyclodextrin molar ratios - constant butane sultone flow rate.

| | β-CD | | BS |
|---|---|---|---|
| Drive speed(rpm) | 11 | 15 | 5 |
| Flow rate(ml/min) | 0.99 | 1.35 | 0.45 |
| Concentration Mol · min ×10$^{-4}$ | 4.36 | 5.94 | $4.4 \times 10^{-3}$ |
| [BS:β-CD] Mole ratio | 10:1 | 7:1 | — |

In addition, the effect of changing the amount of NaOH at a given drive speed/BS:β-CD mole ratio was also carried out, thus obtaining a series of NaOH: CD mole ratios, as shown in FIG. 4. The crude reaction products were dialysed and lyophilized to obtain the sulphobutyl ether of β-CD as a white solid intermediate for chemical analysis. The product was analysed using capillary electrophoresis, mass spectrometry and HPLC to show the degree of substitution, HPLC was carried out to show unreacted β-CD and levels of BS residues were analysed by gas chromatography. The lyophilised product was weighed to give the yield.

Example 1

Figure 3:
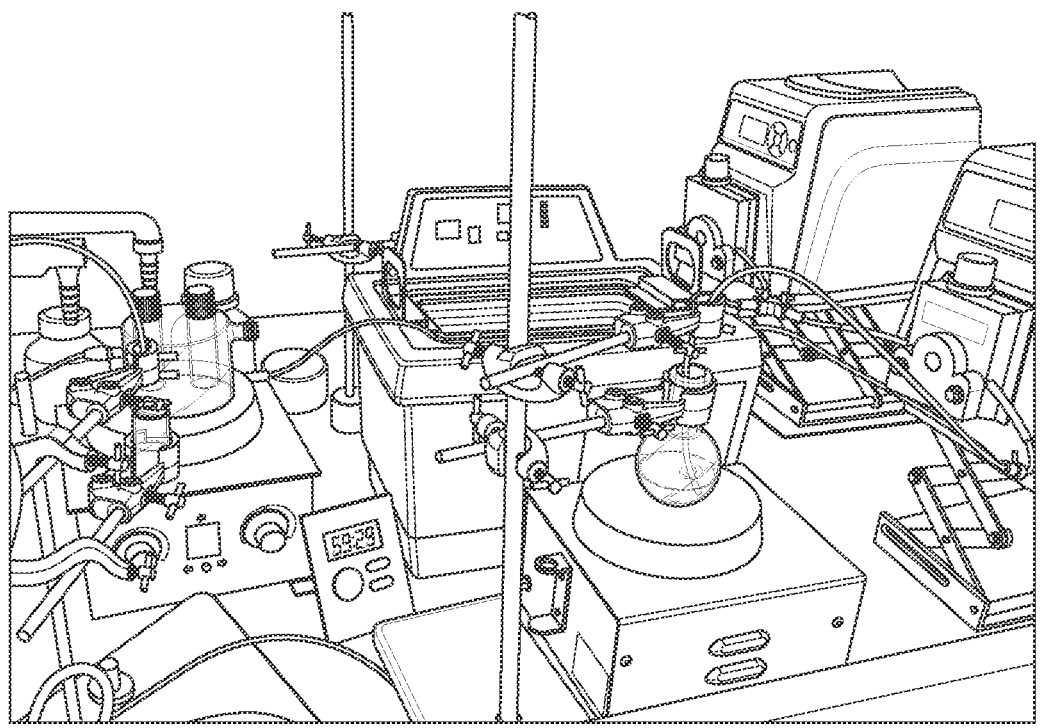
FIG. 3 shows the actual lab-based apparatus for carrying out a continuous flow synthesis for 25 SBE-β-CD.

Referring to FIGS. 2 and 3, there are shown embodiments of the apparatus 2 for the continuous flow synthesis of SBE-β-CD. Two reservoirs (4), (6) are primed, the first reservoir (4) containing "activated" β-cyclodextrin and sodium hydroxide in an aqueous solution, and the second reservoir (6) containing pure 1,4-butane sultone. A first peristaltic pump (8) was turned on to feed the β-cyclodextrin and sodium hydroxide in aqueous solution through a three-way junction (12) with non-return valves. A second peristaltic pump (10) was turned on to feed the 1, 4-butane sultone also through the junction (12) where it reacted with the β-cyclodextrin. The stoichiometry of the reaction could be controlled by mixing the two reaction streams at differential rates, and the ratio of β-cyclodextrin to sodium hydroxide could be adjusted in the reservoir (4) prior to mixing with 1, 4-butane sultone. The amount of SBE-β-CD produced in the process is therefore a function of pumping time, and not equipment scale. The residence time of the reaction between the β-cyclodextrin/NaOH solution and 1, 4-butane sultone was increased by passing the mixture from the outlet of the three-way junction (12) to a holding chamber/sight glass or continuous stirred tank reactor (CSTR) (14) where further reaction took place. The CSTR (14) could be replaced in whole or in part with a temperature controlled coiled tubing of sufficient length. This would provide appropriate level of turbulence and residence time for the coupling reaction to complete efficiently.

The inventors' primary focus was to study the complexity of the sulphoalkylation reaction in the flow synthesis mode. It was therefore necessary to dialyse (18) the reaction effluent (16), freeze dry it (20) and then analyse it (22). Under commercial conditions, the SBE-β-CD effluent (16) leaving the CSTR (14) would be connected to the downstream processing elements, e.g. continuous dialysis, flow-through depyrogenation columns and membrane pre-filters (pore size 0.22 μm or greater) prior to dynamic active pharmaceutical ingredient addition processes described in FIG. 23. The SBE-β-CD produced has been analysed by mass spectrometry, capillary electrophoresis for comparison with the patent literature. The other processing simply becomes an engineering problem as it involves mixing or purification of aqueous SBE-β-CD or SBE-β-CD-drug complex solutions.

Results

Referring to FIGS. 5-20, there are shown electropherograms for the standard batch (standard) and continuous flow (CF) synthesis of SBE-β-CD at the different BS: β-CD molar ratios resulting from differential pump speeds at a constant β-CD: sodium hydroxide mass ratio, or at different β-CD: sodium hydroxide mass ratios for two different BS: β-CD molar ratios as indicated. The standard curve (solid line) corresponds to the known batch manufacture method of SBE-β-CD, as described in U.S. Pat. No. 6,153,746 (Shah et al, 2000). The dotted trace in each graph however is for an SBE-β-CD sample produced by a continuous flow (CF) synthesis process according to the invention.

Referring to FIG. 5, there is shown the electropherograms for SBE-β-CD produced using the known batch method compared to continuous flow (CF) with a 1, 4-Butane Sultone (BS): Beta cyclodextrin (β-CD) drive speed of 3:8 and with a given BS: CD mole ratio as shown in Table 1. As can be seen, there are 10 peaks for the CF method and only 9 peaks for the Batch method. The number of peaks is indicative of the degree of substitution for the derivatives.

Referring to FIG. 6, there is shown the electropherograms for standard sample of Batch produced SBE-β-CD and SBE-β-CD produced by continuous flow synthesis at a 4:8 BS/CD drive speed and therefore a given BS: CD mole ratio as shown in Table 1. As can be seen, there are to peaks for the CF method and only 9 peaks for the Batch method. The number of peaks is indicative of the degree of substitution for the derivatives.

Referring to FIG. 7, there is shown the electropherograms for standard sample of Batch produced SBE-β-CD and SBE-β-CD produced by continuous flow synthesis at a 5:8 BS/CD drive speed, at a given BS: CD mole ratio as shown in Table 1. The two electropherograms show coincidence which indicates equivalence of substitution envelope. Both plots show about 9 distinguishable peaks which correspond to the degree of substitution.

Referring to FIG. 8, there is shown the electropherograms for standard sample of Batch produced SBE-β-CD and SBE-β-CD produced by continuous flow synthesis at a 6:8 BS/CD drive speed at a given BS: CD mole ratio as shown in Table 1. The two electropherograms show coincidence which indicates equivalence of substitution envelope. Both plots show about 9 distinguishable peaks which correspond to the degree of substitution.

Referring to FIG. 9, there is shown the electropherograms for standard sample of Batch produced SBE-β-CD and SBE-β-CD produced by continuous flow synthesis at a 7:8 BS/CD drive speed and at given BS: CD mole ratio as shown in Table 1. The electropherogram for the continuous flow shows an intense peak between 4 and 5 minutes, this peak possibly indicating the presence of a reaction impurity. The BS: β-CD mole ratio indicates an excess of BS.

Referring to FIG. 10o, there is shown the electropherograms for standard sample of Batch produced SBE-β-CD and SBE-β-CD produced by continuous flow synthesis at a 8:8 BS/β-CD drive speed at given BS: CD mole ratio as shown in Table 1. As can be seen, there are 10 peaks for the CF method and only 9 peaks for the Batch method. The number of peaks is indicative of the degree of substitution for the derivatives.

Referring to FIG. 11, there is shown the electropherograms for standard sample of Batch produced SBE-β-CD and SBE-β-CD produced by continuous flow synthesis at a 10:8 BS/CD drive speed at given BS: CD mole ratio as shown in Table 1. The electropherogram for the continuous flow shows an intense peak between 4 and 5 minutes, again this peak possibly indicating the presence of a reaction impurity. The BS: β-CD mole ratio indicates an excess of BS.

Referring to FIG. 12, there is shown the electropherograms for standard sample of Batch produced SBE-β-CD and SBE-β-CD produced by continuous flow synthesis at a 12:8 BS/CD drive speed at given BS: CD mole ratio as shown in Table 1. The electropherogram for the continuous flow also shows an intense peak between 4 and 5 minutes, this peak possibly indicating the presence of a reaction impurity. The BS: β-CD mole ratio indicates an excess of BS.

Referring to FIG. 13, there is shown the electropherograms batch manufactured SBE-β-CD as the solid line and SBE-β-CD manufactured by the continuous flow process with a 7:1 butane sultone to β-cyclodextrin molar ratio as the dotted line. The sodium hydroxide to β-CD molar ratio is 6:1. As can be seen, coincidence of the two electropherograms indicates an equivalent 'Substitution Envelope', i.e. degree of substitution distribution. However, it is remarkable that the continuous flow synthesis process of the invention requires less than 50% of the sodium hydroxide that is used in the prior art batch process (Stella et al, 1994), and a 7:1 molar ratio of 1, 4-butane sultone to β-cyclodextrin instead of the 10:1 used by the prior art method. This finding was completely unexpected, given that the inventors' expectation was at best an equivalent synthetic efficiency. Although the inventors do not wish to be bound by any theory, it would appear that the shielding of sodium hydroxide from 1,4-butane sultone up to the point where the reaction streams mix and the reaction takes place allows for an efficient activation of β-cyclodextrin hydroxyl groups at the point of the reaction with minimal degradation of 1,4-butane sultone to low molecular weight by-products. In short, using the continuous flow method of the invention, 1,4-butane sultone can react with β-cyclodextrin more efficiently and completely to generate higher degrees of substitution with more efficient use of the starting materials.

The average degree of substitution (ADS) can be readily determined using the following formula taken from U.S. Pat. No. 7,635,77B2 (Antle, 2009):—

$$ADS=\Sigma((PAC) \times (MT)/SCA \times 100)/100$$

Where PAC refers to the peak area count; MT refers to the migration time; and SCA refers to the summation of corrected area.

To test this hypothesis further, the inventors attempted to increase the ratio of sodium hydroxide to β-cyclodextrin, and the results are shown in FIGS. 14-20. In the prior art batch process, according to Shah, this would have no beneficial effect on the average degree of substitution or the distribution of low degree of substitution species, i.e. a change in the substitution envelope, because the sodium hydroxide would simply destroy the 1,4-butane sultone before reaction with the hydroxyls could take place. In essence, there is a kinetic limit to the degree of substitution under batch processing conditions. Shah exploits this to maximise the degree of substitution and reduce the residual concentration of reactants.

Referring to FIG. 14, there is shown the electropherograms for standard sample of Batch produced SBE-β-CD and SBE-β-CD sample produced by continuous flow synthesis. As can be seen, the continuous flow uses only 75% sodium hydroxide compared to the amount used in the batch process (Stella et al, 1994), and a 7:1 molar ratio of 1, 4-butane sultone to β-cyclodextrin instead of the 10:1 used by the prior art method. The electropherogram for the continuous flow shows a positive shift of the substitution envelope and change in the modal degree of substitution from ~6 min to 8 min, and this indicates a higher average degree of substitution can be achieved more economically.

Referring to FIG. 15, there is shown there is shown the electropherograms for standard sample of Batch produced SBE-β-CD and SBE-β-CD sample produced by continuous flow synthesis. As can be seen, the continuous flow uses the same amount of sodium hydroxide compared to the amount used in the batch process (Stella et al, 1994), and a 7:1 molar ratio of 1, 4-butane sultone β-cyclodextrin instead of the 10:1 used by the prior art method. The electropherogram for the continuous flow shows a positive shift of the substitution envelope and a further change in the modal degree of substitution from ~6 min to 8.5 min, and this indicates a higher average degree of substitution.

Referring to FIG. 16, there is shown there is shown the electropherograms for standard sample of Batch produced SBE-β-CD and SBE-β-CD sample produced by continuous flow synthesis. As can be seen, the continuous flow uses 25% more sodium hydroxide compared to the amount used in the batch process (Stella et al, 1994), and a 7:1 molar ratio of 1, 4-butane sultone to β-cyclodextrin instead of the 10:1 used by the prior art method. The electropherogram for the continuous flow shows a positive shift of the substitution envelope and further change in the modal degree of substitution from ~6 min to 8 min, very small population of lower degrees of substitution (migration times ~2-7 min), and this indicates a higher degree of substitution.

Referring to FIG. 17 there is shown the electropherograms for standard sample of Batch produced SBE-β-CD and SBE-β-CD sample produced by continuous flow synthesis. As can be seen, the continuous flow uses only 50% sodium hydroxide compared to the amount used in the batch process (Stella et al, 1994), and an increase from 7:1 to 10:1 molar ratio of 1, 4-butane sultone to β-cyclodextrin. As can be seen, there are 10 peaks for the CF method and only 9 peaks for the batch method. The number of peaks is indicative of the distribution of degree of substitution for the derivatives. However, the electropherogram for the continuous flow shows an intense peak at 5 minutes this possibly indicates the presence of a reaction impurity.

Referring to FIG. 18, there is shown the electropherograms for standard sample of Batch produced SBE-β-CD and SBE-β-CD sample produced by continuous flow synthesis. The continuous flow uses only 75% sodium hydroxide compared to the amount used in the batch process (Stella et al, 1994), and an increase from 7:1 to 10:1 molar ratio of 1, 4-butane sultone to β-cyclodextrin. The electropherogram for the continuous flow shows a positive shift of the substitution envelope and change in the modal degree of substitution from ~6 min to 8 min, this indicates a higher average degree of substitution.

Referring to FIG. 19, there is shown there is shown the electropherograms for standard sample of Batch produced SBE-β-CD and SBE-β-CD sample produced by continuous flow synthesis. The continuous flow uses the same amount of sodium hydroxide compared to the amount used in the batch process (Stella et al, 1994), and a 10:1 molar ratio of 1, 4-butane sultone to β-cyclodextrin, identical conditions used by (Stella et al, 1994). The electropherogram for the continuous flow shows a positive shift of the substitution envelope and a change in the modal degree of substitution from ~6 min to 8 min, a smaller population of lower degrees of substitution (migration time range 2-7 minutes) and this indicates a higher degree of substitution. Comparing the electropherogram at identical mole ratios of the material used, the flow method results in species with higher degrees of substitution suggesting a more efficient and hence a more economical production of cyclodextrin.

Referring to FIG. 20, there is shown an electropherogram of batch-produced (Shah et al, 2000) and continuous flow-produced standard SBE-β-CD. The continuous process used to produce the material shown in FIG. 20 used 25% more sodium hydroxide than the batch process (Stella et al, 1994), with an increase in the molar ratio of 1,4-butane sultone to 3-cyclodextrin from 7:1 to 10:1. Hence, the material produced by flow synthesis is novel and demonstrates a positive skew in the Substitution Envelope with a smaller population of lower degrees of substitution (migration time range 2-7 minutes) and the modal degree of substitution changing from ~6 minutes to ~8 minutes. It is concluded therefore that the continuous flow method of the invention results in an increase in efficiency (more efficient activation of 3-cyclodextrin hydroxyl groups by sodium hydroxide; less consumption of 1, 4-butane sultone) resulting in a higher degree of substitution.

A number of experiments were carried out, in order to fully explore the effect of changing the β-CD: sodium hydroxide mass ratio, by altering the sodium hydroxide content between 0% to 200% compared to the amount used in the batch process (Stella et al, 1994). The results of this investigation have been highlighted in Table 3.

TABLE 3

The effect of changing the NaOH:β-CD mole ratio by the changing the NaOH content: 100% nominal sodium hydroxide is equivalent to the base content used in U.S. Pat. No. 5,376,645 (Stella et al, 1994).

| Percentage of NaOH % | NaOH:β-CD mole ratio | Observation (when reacted with butane sultone) |
|---|---|---|
| 0 | — | Very turbid unstable solution with solid white β-CD precipitating out of solution |
| 20 | 2:1 | Less turbid immiscible solution with two layers formed. |
| 25 | 3:1 | Less turbid immiscible solution with two layers formed. |
| 40 | 5:1 | Less turbid immiscible solution with tiny butane sultone particles suspended |
| 50 | 6:1 | Butane sultone reacts with the β-CD solution forming a single phase homogenous solution |
| 75 | 9:1 | Butane sultone reacts with the β-CD solution forming a single phase homogenous solution |
| 100 | 11:1 | Butane sultone reacts with the β-CD solution forming a single phase homogenous solution |
| 125 | 14:1 | Butane sultone reacts with the β-CD solution forming a single phase homogenous solution |
| 150 | 17:1 | Butane sultone reacts with the β-CD solution forming a single phase homogenous solution, solution becoming more viscous |
| 160 | 18:1 | Butane sultone reacts with the β-CD solution forming a single phase homogenous solution, solution becoming more viscous |
| 175 | 20:1 | Butane sultone reacts with the β-CD solution forming a single phase homogenous solution, solution becoming more viscous |
| 200 | 22:1 | Butane sultone reacts with the β-CD solution forming a thick viscous paste |

In the absence of base (i.e. 0% NaOH), β-CD was insoluble and therefore did not react with BS thus precipitating out. At 20-40% NaOH, the two phases would not mix, and β-CD could not react fully with BS. At 150% NaOH, the dialysed product could not be freeze-dried, and also the dialysis membrane was damaged by unreacted butane sultone and the very basic condition arising from high concentrations of sodium hydroxide, hence causing weakening and damaging the membrane. At 200% sodium hydroxide, a viscous paste was formed that prevented pumping of the reaction products. Hence, within the geometry of the apparatus used, 50-125% compared to the amount used in the batch process (Stella et al, 1994), would allow SBE-β-CD to be manufactured using flow chemistry.

Example 2

The first application of SB-β-CD in an injectable pharmaceutical drug product (i.e. voriconazole) is described in the 2003 Pfizer patent, U.S. Pat. No. 6,632,803B1. The formulation of an injectable form of voriconazole is described in Table 4.

TABLE 4

Formulation of an injectable form of voriconazole using the SBE-β-CD platform

| Ingredient or Excipient | Purpose | Concentration in mg/ml in 1 ml of injectable drug product |
|---|---|---|
| Voriconazole | Active Pharmaceutical Ingredient | 10.0 |
| SBE-β-CD | Solubilising Agent | 160.0 |
| Water for Injections | Solvent vehicle | To 1.0 ml |

The manufacturing process is as follows:
1. Add SBE-β-CD to 80% of the final volume of Water for Injections with constant stirring until dissolved;
2. Add the voriconazole and stir until dissolved;
3. Make up the solution to its final volume (hence concentration) with the remaining Water for Injections;
4. Filter the resulting solution through a sterilizing filter (0.22 µm pore size) into a sterile container in a suitably validated GMP manufacturing area;
5. Fill into 20 ml injection vials and stopper; and
6. Freeze-dry the product, stopper, over-cap and label.

The goal of this work was to try and develop innovative approaches to the manufacture and application of SBE-β-CD in the pharmaceutical industry. As can be seen from FIG. 23, use of the method of the invention means that three steps shown in FIG. 22 can be omitted. It is evident on inspection of FIG. 23 that by combining the two processes, three commercial advantages arise:
1. It becomes unnecessary to transport SBE-β-CD from the fine chemical manufacturer to the customer. This would also include warehousing, etc.
2. SBECD could be manufactured on a just-in-time, just-enough basis.
3. One of the two expensive and time-consuming freeze-drying or spray drying process steps could be avoided.

Example 3

The inventors have obtained Vapourtec flow chemistry equipment as illustrated in FIG. 21, which is more suited to commercial manufacture than the 'hand built' reactors used to date. It was necessary to optimise the reaction to meet the specification criteria set out in Shah's patent with respect to residual β-cyclodextrin and 1, 4-butane sultone. In addition, the SBE-β-CD effluent stream was conditioned to meet the requirements of pharmacopoeial Water for Injections monographs.

Example 4

As aqueous solutions of β-CD are intrinsically pyrogenic, the batch process requires depyrogenation as part of the downstream purification. Using this CF manufacturing method, it is possible to depyrogenate the system in reservoir (4) prior to reaction than post reaction.

SUMMARY

The results described herein demonstrated that the continuous flow process chemistry is a more efficient way of producing SBECD and this is reflected in:—
(i) the average degree of substitution,
(ii) the low frequency of low degrees of substituted SBECD species;

(iii) production of SBECD with reduced quantities of starting materials;
(iv) the production of material, free from significant impurities, allowing avoidance of quenching and intensive downstream processing.

The frequency of low degree of substituted SBECD species using the prior art batch reaction is much higher than with using the continuous flow chemistry of the invention. The continuous flow method of the invention enables a greater reaction efficiency. The novel species produced by the continuous flow process have a higher degree of substitution with a tighter distribution of substitution, as well as a higher average degree of substitution per se.

Example 5

The CSTR-Based Manufacturing Process

The aim of this work was to develop a continuous manufacturing process for the manufacture of sulphobutylether β-cyclodextrin. It is known that mixing the β-cyclodextrin and sodium hydroxide in a controlled way is important to the success of the method of the invention. Firstly, it is important that both the aqueous, basified (i.e. activated) β-cyclodextrin solution (4) is heated within the range of 60-90° C. prior to mixing. Secondly, as β-cyclodextrin is added to the sodium hydroxide solution, a three stage 'activation' process occurs:—

1) Firstly, it takes a finite time to add the β-cyclodextrin into the reservoir vessel containing aqueous sodium hydroxide.
2) Next, the β-cyclodextrin dissolves in the sodium hydroxide solution.
3) Finally, and more significantly, an initial solution straw colouration progressively 'deepens' which is considered to be a sign of completion of the activation of the 3-cyclodextrin by sodium hydroxide. With the deep colouration present, and the reagents at the specified temperature, mixing then proceeds.

The reaction proceeds in a continuous manner, i.e. once the pumps (8, 10) have started they are not switched off until completion of the reaction. It is now generally considered that the main reaction takes place in the first CSTR chamber (14). The reaction takes place at a low temperature (65-100° C.) and atmospheric pressure. The CSTR-process handles the β-cyclodextrin-sodium hydroxide solutions and butane sultone as an immiscible, two phase system.

It is known that some prior art methods create the conditions where butane sultone and the aqueous β-cyclodextrin-sodium hydroxide streams may become miscible; miscibility is generally considered to be an important process condition of flow chemistry processing. Judging by the Average Degrees of Substitution achieved by prior art methods, the goal of miscibility appears to have been achieved at the expense of butane sultone stability which has led to very low Average Degrees of Substitution.

The method of the invention however involves carefully reacting sodium hydroxide with 3-cyclodextrin to activate it in advance of a two-phase continuous flow reaction, and this is important in creating a highly efficient reaction and a controllable Average Degree of Substitution in a small footprint. The activation process must be conducted at elevated temperature (65-100° C.) and for a specified time after the β-cyclodextrin has dissolved in the aqueous sodium hydroxide solution. The activation process has typically taken 30 minutes at this scale; the major indicator of completion is the colour change which could be measured colourimetrically.

It is highly unlikely that this time and temperature dependent activation could be achieved in any prior art batch or continuous flow methods. Whilst the reaction procedure employs a CSTR, it is a surrogate for the use of a flow reactor with efficient mixing and of suitable length to allow the reaction to complete within the reactor tubing. The activation of β-cyclodextrin is an important process parameter prior to reaction and this must continue irrespective of the reactor architecture.

Example 6

Analytical Methodology for High Degree of Substitution SBECD Species

The original work described herein was based on the capillary electrophoresis method for sulphobutylether β-cyclodextrin described in the United States Pharmacopoeia 35/National Formulary 30 (USP35/NF30). The output of the analysis, the so-called electropherogram, is shown in FIGS. 5-20.

It can be seen that, whilst a qualitative idea of the substitution pattern is possible, it is not easy to integrate the areas under the peaks reliably due to the shifting baseline. It is also evident from FIG. 14-16 and 18-20 that peak resolution deteriorates with increasing substitution. Peaks appear to merge after approximately 8 minutes into the run which makes it difficult to quantify the pattern of substitution. Furthermore, the true nature of the substitution envelope could not be clearly understood.

Alternative methods have been proposed for the analysis of cyclodextrin derivatives using high performance liquid chromatography (J. Szeman 2006). This has been recently updated and applied to sulphobutylether β-cyclodextrin (J. Szeman 2012). The method is based on a specialised ion-exchange HPLC column, CD-Screen-DAP, where a bonded dimethylamino phenyl function includes in the eluting sulphobutylether β-cyclodextrin to improve the selectivity of the analytical method.

High performance liquid chromatography with evaporative light scattering detection (ELSD) is used for the separation of sulphobutylether β-cyclodextrin into its substituted constituents in order to determine the average degree of substitution. Identification of each substituted cyclodextrin is determined by comparing the retention times of the standard, produced by the method described in U.S. Pat. No. 6,153,746 (Shah, 2000), and tested according to the methods described in USP35/NF30 with that of a material produced using the processing method described herein.

The chromatographic conditions are summarised as follows:

Reagents
1. Acetonitrile, HPLC grade
2. 0.5% triethylamine-acetic acid buffer, pH=5.0

Chromatographic Conditions

| | |
|---|---|
| Instrument: | Agilent 1100 series or equivaent HPLC instrument |
| Software: | OpenLAB or similar system |
| Column: | CD-Screen-DAP, 3 μm, 150 × 4.0 mm, CDS-DAP-1504-03 |
| Column temperature: | 25° C. ± 1° C. |
| Mobile phase A (MPA): | 0.5% triethylamine-acetic acid buffer, pH = 5 |
| Mobile phase B (MPB): | acetonitrile, HPLC grade |
| Flow rate: | 1.0 ml/min |

-continued

| Gradient Ratio | Time (min) | 0 | 6 | 15 |
|---|---|---|---|---|
| | MPA (%) | 100 | 50 | 50 |
| | MPB (%) | 0 | 50 | 50 |
| Detection: | ELSD | | | |
| Injection volume: | 5 µl | | | |
| Concentration: | 10 mg/ml | | | |
| Acquisition time: | 15 minutes with post-time of 5 minutes | | | |
| Needle wash: | none | | | |

ELSD Conditions

| Instrument: | Alltech ELSD 2000 or equivalent ELSD instrument |
|---|---|
| Tube temperature: | 115° C. |
| Gas flow (nitrogen): | 3.2 L/min |
| Gain: | 2 |
| Impactor: | Off |

A typical chromatogram for the standard material produced using a prior art batch method described in U.S. Pat. No. 6,153,746 (Shah, 2000) is shown in FIG. 24. Upon further examination of FIG. 24, it can be seen that material produced by the prior art process has a range of substitution from Degree of Substitution 2 to 10. The Average Degree of Substitution is 6.6.

The chromatogram for the sulphobutylether β-cyclodextrin produced using the method of the to invention and corresponding to FIG. 20 is shown in FIG. 25. It is readily seen that a stable baseline is generated facilitating integration and subsequent processing of the signal. FIG. 25 indicates that material produced using the invention has a range of substitution from Degree of Substitution 3 to 13. The Average Degree of Substitution is 10.4, as described below.

In addition to producing sulphobutylether β-cyclodextrin with a higher Average Degree of Substitution, the method of the invention, under these conditions, does not produce any detectable di-substituted sulphobutylether β-cyclodextrin and produces significant quantities of Degree of Substitution 11-13 not detected in the U.S. Pat. No. 6,153,746 (Shah, 2000) material.

The inventors also have the corresponding HPLC traces corresponding to the electropherograms in FIGS. 12 to 20. The power of the technique gives access to descriptive statistics.

The Average Degree of Substitution is discussed herein using the standard method of calculation. This method was modified for use with HPLC outputs and is explained below.

The Individual Degree of Substitution ($IDS_n$) is calculated using the following formula:

$$IDS_n = (PA_n / \Sigma PA) \times 100 \qquad (1)$$

$$\text{where } \Sigma PA = \Sigma PA_L + PA_{L+1} \ldots PA_H \qquad (2)$$

n=Substitution Number
PA=Peak area
$PA_L$=Peak area corresponding to lowest degree of substitution seen on the chromatogram
$PA_H$=Peak area corresponding to highest degree of substitution seen on the chromatogram These data can be used to describe an 'Envelope of Substitution' which is used as the basis of a specification element in USP35/NF30, where each $IDS_n$ should fall within the series of specified Proven Acceptable Ranges thus defining the 'Substitution Envelope'.

The Individual Degree of Substitution metrics are then used to calculate the Average Degree of Substitution as follows:

$$ADS = \Sigma(IDS_n \times n) / 100 \qquad (3)$$

Table 1 shows data for the chromatogram shown in FIG. 25. This can now be processed using Equations 1-3 as follows:

TABLE 1

Integration table of the chromatogram of sulphobutylether β-cyclodextrin produced by the method of the invention. Reaction conditions correspond to those used to generate FIG. 20 HPLC conditions are based on a gradient separation with a CD-Screen-DAP column and ELSD detection

| Substitution Number: | Retention Time: | Peak Area: |
|---|---|---|
| 3 | 5.77 | 0.271 |
| 4 | 6.29 | 0.507 |
| 5 | 6.67 | 1.455 |
| 6 | 6.98 | 3.142 |
| 7 | 7.33 | 5.221 |
| 8 | 7.63 | 13.283 |
| 9 | 7.99 | 24.842 |
| 10 | 8.31 | 46.056 |
| 11 | 8.58 | 53.920 |
| 12 | 8.90 | 39.220 |
| 13 | 9.28 | 16.570 |

Individual Degree of Substitution—Specimen Calculation $\Sigma PA = \Sigma PA_L + PA_{L+1} \ldots PA_H$ $\Sigma PA = PA_3 + PA_4 + PA_5 + PA_6 + PA_7 + PA_8 + PA_9 + PA_{10} + PA_{11} + PA_{12} + PA_{13}$ $\Sigma PA = 0.271 + 0.507 + 1.455 + 3.142 + 5.221 + 13.283 + 24.842 + 46.056 + 53.920 + 39.220 + 16.570$ $\Sigma PA = 204.487$ $IDS_n = (PA_n / \Sigma PA) \times 100$ $IDS_3 = (PA_3 / \Sigma PA) \times 100 = (0.271 / 204.487) \times 100 = 0.132527$ $IDS_4 = (PA_4 / \Sigma PA) \times 100 = (0.507 / 204.487) \times 100 = 0.247938$ $IDS_5 = (PA_5 / \Sigma PA) \times 100 = (1.455 / 204.487) \times 100 = 0.711537$ $IDS_6 = (PA_6 / \Sigma PA) \times 100 = (3.142 / 204.487) \times 100 = 1.536528$ $IDS_7 = (PA_7 / \Sigma PA) \times 100 = (5.221 / 204.487) \times 100 = 2.553219$ $IDS_8 = (PA_8 / \Sigma PA) \times 100 = (13.283 / 204.487) \times 100 = 6.495767$ $IDS_9 = (PA_9 / \Sigma PA) \times 100 = (24.842 / 204.487) \times 100 = 12.14845$ $IDS_{10} = (PA_{10} / \Sigma PA) \times 100 = (46.056 / 204.487) \times 100 = 22.5277$ $IDS_{11} = (PA_{11} / \Sigma PA) \times 100 = (53.920 / 204.487) \times 100 = 26.36842$ $IDS_{12} = (PA_{12} / \Sigma PA) \times 100 = (39.220 / 204.487) \times 100 = 19.1797$ $IDS_{13}=(PA_{13}/\Sigma PA)\times 100=(16.570/204.487)\times 100=8.103205$ Average Degree of Substitution—Specimen Calculation $ADS=\Sigma(IDS_n\times \text{substitution number})/100$ n=substitution number $IDS_n\times \text{substitution number}$ $IDS_3\times 3=0.132527\times 3=0.397580$ $IDS_4\times 4=0.247938\times 4=0.991750$ $IDS_5\times 5=0.711537\times 5=3.557683$ $IDS_6\times 6=1.536528\times 6=9.219168$ $IDS_7\times 7=2.553219\times 7=17.872530$ $IDS_8\times 8=6.495767\times 8=51.966140$ $IDS_9\times 9=12.14845\times 9=109.336046$ $IDS_{10}\times 10=22.5277\times 10=225.227032$ $IDS_{11}\times 11=26.36842\times 11=290.052668$ $IDS_{12}\times 12=19.1797\times 12=230.156440$ $IDS_{13}\times 13=8.103205\times 13=105.341660$ $\Sigma(IDS_n\times \text{substitution number})=(IDS_3\times 3)+(IDS_4\times 4)+(IDS_5\times 5)+(IDS_6\times 6)+(IDS_7\times 7)+(IDS_8\times 8)+(IDS_9\times 9)+(IDS_{10}\times 10)+(IDS_{11}\times 11)+(IDS_{12}\times 12)+(IDS_{13}\times 13)$ $\Sigma(IDS_n\times \text{substitution number})=0.397580+0.991750+3.557683+9.219168+17.872530+51.966140+109.336046+225.227032+290.052668+230.156440+105.341660$ $\Sigma(IDS_n\times \text{substitution number})=1044.118697$ $ADS=\Sigma(IDS_n\times \text{substitution number})/100=1044.118697/100=10.44$ Average Degree of Substitution=10.4

The material described in FIG. 25 therefore has an average degree of substitution of 10.4, which is substantially higher than material produced by batch manufacture or fully continuous flow process.

Example 7

The Manipulation of Average Degree of Substitution Using Sodium Hydroxide

The samples of sulphobutylether β-cyclodextrin that have been produced have now been reanalysed by HPLC. The data has been processed to generate the Average Degrees of Substitution. The table shown in FIG. 26 shows a summary of the data adding the Average to Degree of Substitution data and dispersion data.

In general, it can be seen from the Table in FIG. 26 that an increase in the content of sodium hydroxide will increase the Average Degree of Substitution of sulphobutylether β-cyclodextrin.

Furthermore, the more extreme CSTR reactions produce material with Average Degree of Substitution at levels not previously seen using batch or continuous flow reactions. The higher Average Degree of Substitution arises due to the presence of highly substituted species with an Individual Degree of Substitution in excess of 10.

The table shown in FIG. 27 describes an attempt to produce material compliant with the USP35/NF30 monograph with the use of more moderate reaction conditions. Analysis indicated that the $IDS_n$ 'envelope' present in the CSTR 10:1 butane sultone: β-cyclodextrin molar ratio and a 6:1 Sodium hydroxide to β-cyclodextrin molar ratio reaction produced the nearest match. It can be seen that, using the HPLC method, the U.S. Pat. No. 6,153,746 (Shah, 2000) material broadly complies with the specification. The material produced by the CSTR method is less compliant due to a more symmetrical distribution of $IDS_n$. Whilst compliant material has yet to be produced, the ability to control the process with respect to stoichiometry indicates that, with further process refinement, this should be possible.

Example 8

Novelty of SBE-β-CD Prepared Using the Method of the Invention

Historically, the number of pendant sulphobutyl groups on the cyclodextrin determines the Individual Degree of Substitution metric and the Substitution Envelope. The weighted average of the abundance of each species gives rise to the Average Degree of Substitution metric. There are three possibilities for defining the novelty of the SBE-β-CD prepared using the method of the invention:

a) Substitution

What is really important, chemically, is the number of cyclodextrin rings available to form inclusion complexes with drugs, because this is what makes the cyclodextrin work. Whilst the parent beta cyclodextrin gives the greatest number of rings for a given molecular mass, it is believed to be nephrotoxic and this makes substitution necessary. It is known that increasing the degree of substitution increases the aqueous solubility of the cyclodextrin and high solubility of the cyclodextrin is a pre-requisite to achieving a high payload drug solubility. The following table summarises substitution molecular mass ratios:

| IDS | Beta cyclodextrin Molecular Weight | Proton Loss | Molecular Weight After Proton Loss | Butane sultons Group Contribution | Molecular Weight for IDS | Substitution Molecular Mass Fraction |
|---|---|---|---|---|---|---|
| 1 | 1134.98 | −1 | 1133.98 | 136.17 | 1270.15 | 0.11 |
| 2 | 1134.98 | −2 | 1132.98 | 272.34 | 1405.32 | 0.19 |
| 3 | 1134.98 | −3 | 1131.98 | 408.51 | 1540.49 | 0.26 |
| 4 | 1134.98 | −4 | 1130.98 | 544.68 | 1675.66 | 0.32 |
| 5 | 1134.98 | −5 | 1129.98 | 680.85 | 1810.83 | 0.37 |
| 6 | 1134.98 | −6 | 1128.98 | 817.02 | 1946.00 | 0.42 |
| 7 | 1134.98 | −7 | 1127.98 | 953.19 | 2081.17 | 0.45 |
| 8 | 1134.98 | −8 | 1126.98 | 1089.36 | 2216.34 | 0.49 |
| 9 | 1134.98 | −9 | 1125.98 | 1225.53 | 2351.51 | 0.52 |

-continued

| IDS | Beta cyclodextrin Molecular Weight | Proton Loss | Molecular Weight After Proton Loss | Butane sultons Group Contribution | Molecular Weight for IDS | Substitution Molecular Mass Fraction |
|---|---|---|---|---|---|---|
| 10 | 1134.98 | −10 | 1124.98 | 1361.70 | 2486.68 | 0.54 |
| 11 | 1134.98 | −11 | 1123.98 | 1497.87 | 2621.85 | 0.57 |
| 12 | 1134.98 | −12 | 1122.98 | 1634.04 | 2757.02 | 0.59 |
| 13 | 1134.98 | −13 | 1121.98 | 1770.21 | 2892.19 | 0.61 |

The molecular mass of beta cyclodextrin is 1134.98 Dalton. To create a mono-substituted beta cyclodextrin, a proton is removed, and replaced with a linear butane sultone function with a molecular mass of 136.17 Dalton. The resulting molecular mass of individual degree of substitution (IDS), where n=1 is 1270.15 Dalton. If one considers the mass associated with the cyclodextrin ring as a fraction of the total mass, it is possible to calculate a Substitution Molecular Mass Fraction. This means that 11% of the mass is associated with the substituent functions (or 89% is associated with the cyclodextrin ring function). The table shows these values up to the SBE-β-CD prepared using the method of the invention, having a surprisingly high IDS=13 species.

The values of individual degree of substitution (IDS) and Substitution Molecular Mass Fraction (SMF) shown in the above table have been plotted out on FIG. 28, and the relationship can be seen. The inventors believe that, to date, SBE-R-CD with an SMF greater than 0.57 has not been previously reported, and as such the composition is novel per se.

b) Molecular Weight

This is the first report of a derivatised species with a molecular weight in excess of 2486.68 Dalton or within the range 2621.85-2892.19. Referring to FIG. 29, there is shown the relationship between individual degree of substitution and molecular weight.

Molecular weight is believed to be an alias for Individual Degree of Substitution and so the Substitution Molecular Mass Fraction (SMF) may be the better choice.

c) Substitution Envelope

When considering Column 2 of FIG. 27, it is possible to define a novel peak area limit as follows:

The USP-NF Peak Area Percentage describes a series of Proven Acceptable Ranges for an upper and lower distribution of IDSn in which a 'Substitution Envelope' resides. With a shift in IDSn to higher values using the process of the invention, it is possible to shift the envelope. As shown in FIG. 27, it is possible to 'de-tune' the process of the invention to broadly comply with the USP-NF Envelope, and this is not possible using the fully batch or fully continuous processes described in the prior art.

SUMMARY

Using a novel, improved HPLC analytical method, the inventors have validated their earlier observations described herein. The technique has allowed them to produce descriptive statistics for high degree of substitution material. The sulphobutylether β-cyclodextrin composition, produced by the CSTR process according to the invention described herein, is novel in two respects: (i) it has an unprecedented high average degree of substitution; and (ii) the existence of highly substituted species with $IDS_n$ higher than 10. The CSTR process depends upon pre-activation of the β-cyclodextrin feedstock by sodium hydroxide where the extent of activation determines the Average Degree of Substitution. The process allows control of Average Degree of Substitution by varying the sodium hydroxide concentration. The process can be used to produce material with a high Average Degree of Substitution. It will be possible to manufacture material compliant with the USP35/NF30 specification for sulphobutylether β-cyclodextrin. The process enables the production of sulphobutylether β-cyclodextrin on a 'just in time', 'just enough' basis in a small manufacturing footprint.

| IDSn | USP-NF Peak Area Percentage Lower Limit | USP-NF Peak Area Percentage Upper Limit | Range | Shah | Novel Peak Area Percentage Lower Limit | Novel Peak Area Percentage Upper Limit | Range | CSTR 10:1 and +25% |
|---|---|---|---|---|---|---|---|---|
| 1 | 0.00 | 0.30 | 0.30 | 0.00 | 0.00 | 0.00 | 0.00 | 0.00 |
| 2 | 0.00 | 0.90 | 0.90 | 0.13 | 0.00 | 0.00 | 0.00 | 0.00 |
| 3 | 0.50 | 5.00 | 4.50 | 0.88 | 0.00 | 0.30 | 0.30 | 0.10 |
| 4 | 2.00 | 10.00 | 8.00 | 4.91 | 0.00 | 0.90 | 0.90 | 0.20 |
| 5 | 10.00 | 20.00 | 10.00 | 14.61 | 0.50 | 5.00 | 4.50 | 0.70 |
| 6 | 15.00 | 25.00 | 10.00 | 25.45 | 0.50 | 5.00 | 4.50 | 1.50 |
| 7 | 20.00 | 30.00 | 10.00 | 29.50 | 0.50 | 5.00 | 4.50 | 2.60 |
| 8 | 10.00 | 25.00 | 15.00 | 19.01 | 2.00 | 10.00 | 8.00 | 6.50 |
| 9 | 2.00 | 12.00 | 10.00 | 4.99 | 10.00 | 20.00 | 10.00 | 12.10 |
| 10 | 0.00 | 4.00 | 4.00 | 0.51 | 15.00 | 25.00 | 10.00 | 22.50 |
| 11 | 0.00 | 0.00 | 0.00 | 0.00 | 20.00 | 30.00 | 10.00 | 26.40 |
| 12 | 0.00 | 0.00 | 0.00 | 0.00 | 10.00 | 25.00 | 15.00 | 19.20 |
| 13 | 0.00 | 0.00 | 0.00 | 0.00 | 2.00 | 12.00 | 10.00 | 8.10 |
| 14 | 0.00 | 0.00 | 0.00 | 0.00 | 0.00 | 4.00 | 4.00 | 0.00 |

REFERENCES

J. Szeman, K. Csabai, K. Kekesi, L. Szente, G. Varga. "Novel stationary phases for high-performance liquid chromatography." *Journal of Chromatography A*, 2006: 76-82.

J. Szeman, T. Sohajda, E. Olah, E. Varga, K. Csabai, G. Varga, L. Szente. "Characterization of Randomly Substituted Anionic Cyclodextrin Derivatives with Different Analytical Methods." 16*th International Cyclodextrin Symposium*. Tianjin, China, 2012.

All publications, patents, and patent applications cited in this specification are herein incorporated by reference as if each individual publication, patent, or patent application were specifically and individually indicated to be incorporated by reference. The following United States Provisional Patent Application is specifically incorporated by reference herein: U.S. 61/847,509 entitled "CYCLODEXTRIN" filed 17 Jul. 2013. The following United Kingdom Patent Application is specifically incorporated by reference herein: GB 1312737.8 filed 17 Jul. 2013.

The invention claimed is:

1. A composition comprising sulphobutyl ether β-cyclodextrin (SBE-β-CD), wherein the average degree of substitution (ADS) is 7.3 or more and the composition comprises a range of individual degrees of substitution.

2. A composition according to claim 1, wherein the sulphobutyl ether β-cyclodextrin (SBE-β-CD) is produced by contacting cyclodextrin with a base to form activated cyclodextrin, and separately contacting the activated cyclodextrin with an alkyl sultone to form sulphoalkyl ether-β-cyclodextrin, wherein the sulphoalkylation reaction is carried out under continuous flow conditions.

3. A composition according to claim 1, wherein the composition comprises SBE-β-CD having a Substitution Molecular Mass Fraction (SMF) greater than 0.57.

4. A drug delivery system comprising the sulphobutyl ether β-cyclodextrin according to claim 1.

5. The drug delivery system according to claim 4, wherein the drug delivery system is an excipient, which exhibits little or no side effects with regard to renal physiology.

6. A pharmaceutical excipient comprising the sulphobutyl ether β-cyclodextrin according to claim 1.

7. A composition accordingly to claim 1, wherein the average degree of substitution (ADS) is 8 or more.

8. A composition accordingly to claim 1, wherein the average degree of substitution (ADS) is 9 or more.

9. A composition accordingly to claim 1, wherein the average degree of substitution (ADS) is 10 or more.

10. A composition according to claim 1, wherein the composition comprises SBE-β-CD having a Substitution Molecular Mass Fraction (SMF) greater than 0.58.

11. A composition according to claim 1, wherein the composition comprises SBE-β-CD having a Substitution Molecular Mass Fraction (SMF) greater than 0.59.

\* \* \* \* \*